(12) United States Patent
Kobayashi et al.

(10) Patent No.: US 11,375,899 B2
(45) Date of Patent: Jul. 5, 2022

(54) IMAGE CAPTURING APPARATUS AND BIOMETRIC INFORMATION ACQUIRING APPARATUS

(71) Applicants: RIKEN, Saitama (JP); DCT CO., LTD., Tokyo (JP)

(72) Inventors: Takuma Kobayashi, Saitama (JP); Hitoshi Okamoto, Saitama (JP); Hiroyuki Iino, Tokyo (JP); Kazushige Ooi, Tokyo (JP)

(73) Assignees: RIKEN, Saitama (JP); DCT CO., LTD., Tokyo (JP)

( * ) Notice: Subject to any disclaimer, the term of this patent is extended or adjusted under 35 U.S.C. 154(b) by 897 days.

(21) Appl. No.: 16/120,429

(22) Filed: Sep. 3, 2018

(65) Prior Publication Data

US 2019/0014985 A1 Jan. 17, 2019

Related U.S. Application Data

(63) Continuation-in-part of application No. PCT/JP2017/008620, filed on Mar. 3, 2017.

(30) Foreign Application Priority Data

Mar. 4, 2016 (JP) .............................. JP2016-042550

(51) Int. Cl.
*A61B 5/00* (2006.01)
*G01N 21/64* (2006.01)

(52) U.S. Cl.
CPC .......... *A61B 5/0071* (2013.01); *A61B 5/0077* (2013.01); *A61B 5/0084* (2013.01);
(Continued)

(58) Field of Classification Search
CPC . A61B 5/0071; A61B 5/0077; G01N 21/6456
See application file for complete search history.

(56) References Cited

U.S. PATENT DOCUMENTS

| 5,827,172 A | 10/1998 | Takahashi | |
|---|---|---|---|
| 2004/0240048 A1* | 12/2004 | Dietrich | G02B 21/20 359/368 |

(Continued)

FOREIGN PATENT DOCUMENTS

| JP | 2005027851 A | 2/2005 |
|---|---|---|
| JP | 2006292412 A | 10/2006 |

(Continued)

OTHER PUBLICATIONS

Kunal K Ghosh et al., "Miniaturized integration of a fluorescence microscope," Nature Methods, Oct. 2011, vol. 8, No. 10, p. 871-878.

(Continued)

*Primary Examiner* — Jason M Ip

(57) ABSTRACT

Provided is a light detecting apparatus comprising a light emitting section that emits light; a light detecting section that detects light from an observation target irradiated with the light emitted by the light emitting section; a mount section attached to a test subject that includes the observation target; and a holding section that holds the light emitting section and the light detecting section and is detachably attached to the mount section. The holding section holds the light emitting section and the light detecting section in a manner to secure a relative positional relationship between the light emitting section and the light detecting section, and a relative positional relationship between the holding section and the mount section is determined by attaching the holding section to the mount section.

18 Claims, 20 Drawing Sheets

(52) U.S. Cl.
CPC .......... *A61B 5/6803* (2013.01); *A61B 5/6805* (2013.01); *G01N 21/6456* (2013.01); *A61B 5/0042* (2013.01); *A61B 5/7217* (2013.01); *A61B 2503/40* (2013.01); *A61B 2503/42* (2013.01); *G01N 2201/0634* (2013.01)

(56) References Cited

U.S. PATENT DOCUMENTS

| | | | |
|---|---|---|---|
| 2006/0238885 A1* | 10/2006 | Hasegawa | G02B 21/33 359/657 |
| 2007/0213592 A1 | 9/2007 | Yamada | |
| 2011/0257488 A1 | 10/2011 | Koyama | |
| 2014/0355003 A1 | 12/2014 | Masumura | |
| 2015/0309295 A1 | 10/2015 | Cocker | |
| 2015/0316488 A1 | 11/2015 | Masumura | |

FOREIGN PATENT DOCUMENTS

| | | |
|---|---|---|
| JP | 2007151748 A | 6/2007 |
| JP | 2012095803 A | 5/2012 |

OTHER PUBLICATIONS

A. Paul Alivisatos et al.., "Nanotools for Neuroscience and Brain Activity Mapping," ACS Nano, 2013, vol. 7, No. 3, p. 1850-1866.
Karl Deisseroth et al., "Engineering Approaches to Illuminating Brain Structure and Dynamics," Neuron, Oct. 30, 2013, vol. 80, p. 568-577.
Elizabeth J.O.Hamel et al., "Cellular Level Brain Imaging in Behaving Mammals: An Engineering Approach," Neuron, Apr. 8, 2015, vol. 86, p. 140-159.
Yaniv Ziv et al., "Miniature microscopes for large-scale imaging of neuronal activity in freely behaving rodents," Current Opinion in Neurobiology, 2015, vol. 32, p. 141-147.
Joshua H.Jennings et al., "Visualizing Hypothalamic Network Dynamics for Appetitive and Consummatory Behaviors," Cell, Jan. 29, 2015, vol. 160, p. 516-527.
J.Nicholas Betley et al., "Neurons for hunger and thirst transmit a negative-valence teaching signal," Nature, May 14, 2015, vol. 521, p. 180-185.
Kartikeya Murari et al., "An Integrated Imaging Microscope for Untethered Cortical Imaging in Freely-moving Animals," 32nd Annual International Conference of the IEEE EMBS, Aug. 31-Sep. 4, 2010, p. 5795-5798.
"Simultaneous Multilayer Cortical Imaging with Prism Probes," Inscopix Solutions, Inscopix, 2015, p. 1-4.
Joon Hyuk Park et al., "Head-mountable high speed camera for optical neural recording," Journal of Neuroscience Methods, 2011, vol. 201, p. 290-295.
Hang Yu et al., "Miniaturized optical neuroimaging in unrestrained animals," NeuroImage, 2015, vol. 113, p. 397-406.
International Search Report for International Patent Application No. PCT/JP2017/008620, issued by the Japan Patent Office dated Apr. 4, 2017.
Oliver Skocek et al.., "High-speed volumetric imaging of neuronal activity in freely moving rodents", Nature Methods, Nature America Inc., vol. 15, pp. 429-432, May 7, 2018.
International Preliminary Report on Patentability for International Application No. PCT/JP2017/008620, issued by the International Bureau of WIPO dated Sep. 4, 2018.
Portable LED Kenbikyo Bairitsu 100-bai PVC+LED Watt/Crystal Lens Kenbikyo Kobairitsu ISM-MG10085 Shohin Shokai Page, amazon [online], Dec. 4, 2015 (Dec. 4, 2015) [retrieval date Mar. 17, 2017 (Mar. 17, 2017)], Internet<https://www.amazon.co.jp/dp/B018XBLL4Q/>.

* cited by examiner

IMAGE CAPTURING APPARATUS AND BIOMETRIC INFORMATION ACQUIRING APPARATUS

The contents of the following Japanese patent application and PCT patent application are incorporated herein by reference:
NO. 2016-042550 filed on Mar. 4, 2016, and
NO. PCT/JP2017/008620 filed on Mar. 3, 2017.

BACKGROUND

1. Technical Field

The present invention relates to an imaging apparatus and a biometric information acquiring apparatus.

2. Related Art

In recent years, research has been conducted about systems that gather information generated within living tissue by irradiating the living tissue with light while applying stimulation to the living tissue and capturing fluorescent light images from the living tissue, for example, as shown in Patent Document 1 and the Non-Patent Documents below.

Patent Document 1: Japanese Patent Application Publication No. 2012-95803

Non-Patent Document 1: Kunal K Ghosh et. al., "Miniaturized integration of a fluorescence microscope," *NATURE METHODS*, October 2011, Vol. 8, No. 10, p. 871-878

Non-Patent Document 2: A. Paul Alivisatos et. al., "Nanotools for Neuroscience and Brain Activity Mapping," *ACS NANO*, 2013, Vol. 7, No. 3, p. 1850-1866

Non-Patent Document 3: Karl Deisseroth et. al., "Engineering Approaches to Illuminating Brain Structure and Dynamics," Neuron, Oct. 30, 2013, Vol. 80, p. 568-577

Non-Patent Document 4: Elizabeth J. O. Hamel et. al., "Cellular Level Brain Imaging in Behaving Mammals: An Engineering Approach," *Neuron, Apr.* 8, 2015, Vol. 86, p. 140-159

Non-Patent Document 5: Yaniv Ziv et. al., "Miniature microscopes for large-scale imaging of neuronal activity in freely behaving rodents," *Current Opinion in Neurobiology*, 2015, Vol. 32, p. 141-147

Non-Patent Document 6: Joshua H. Jennings et. al., "Visualizing Hypothalamic Network Dynamics for Appetitive and Consummatory Behaviors," *Cell, Jan.* 29, 2015, Vol. 160, p. 516-527

Non-Patent Document 7: J. Nicholas Betley et. al., "Neurons for hunger and thirst transmit a negative-valence teaching signal," *Nature, May* 14, 2015, Vol. 521, p. 180-185

Non-Patent Document 8: Kartikeya Murari et. al., "An Integrated Imaging Microscope for Untethered Cortical Imaging in Freely-moving Animals," 32nd Annual International Conference of the IEEE EMBS, Aug. 31-Sep. 4, 2010, p. 5795-5798

Non-Patent Document 9: "Simultaneous Multilayer Cortical Imaging with Prism Probes," *Inscopix Solutions*, Inscopix, 2015, p. 1-4

Non-Patent Document 10: Joon Hyuk Park et. al., "Headmountable high speed camera for optical neural recording," *Journal of Neuroscience Methods*, 2011, Vol. 201, p. 290-295

Non-Patent Document 11: Hang Yu et. al., "Miniaturized optical neuroimaging in unrestrained animals," *NeuroImage*, 2015, Vol. 113, p. 397-406

A conventional imaging system, even when miniaturized, has dimensions of approximately 15 mm×14 mm×20 mm and a weight of approximately 3 g.

SUMMARY

According to a first aspect of the present invention, provided is a light detecting apparatus. The light detecting apparatus comprises a light emitting section that emits light. The light detecting apparatus comprises a light detecting section that detects light from an observation target irradiated with the light emitted by the light emitting section. The light detecting apparatus comprises a mount section attached to a test subject that includes the observation target. The light detecting apparatus comprises a holding section that holds the light emitting section and the light detecting section and is detachably attached to the mount section. In the light detecting apparatus, the holding section holds the light emitting section and the light detecting section in a manner to secure a relative positional relationship between the light emitting section and the light detecting section. In the light detecting apparatus, a relative positional relationship between the holding section and the mount section is determined by attaching the holding section to the mount section.

In the light detecting apparatus, at least one of the holding section and the mount section may include a positioning section that determines the relative positional relationship between the holding section and the mount section when the holding section is attached to the mount section. In the light detecting apparatus, a cavity or light guiding member penetrating through the mount section may be arranged inside the mount section. In the light detecting apparatus, the light emitting section may be arranged such that the light from the light emitting section passes through the cavity or the light guiding member, is emitted from a surface of the mount section facing the observation target, and arrives at the observation target. In the light detecting apparatus, the light detecting section may be arranged such that the light from the observation target is incident to the cavity or the light guiding member from the surface of the mount section facing the observation target, passes through the cavity or the light guiding member, and arrives at the light detecting section. In the light detecting apparatus, the relative positional relationship between the light emitting section and the light detecting section may be determined such that reflected light, which is light from the light emitting section reflected inside the cavity or the light guiding member does not directly arrive at the light detecting section.

In the light detecting apparatus, the cavity may be arranged inside the mount section, and at least one of the light emitting section and the light detecting section may be arranged inside the cavity. In the light detecting apparatus, the cavity may be arranged inside the mount section, and an opening for inserting a tool inside the cavity from outside the mount section may be formed in the mount section.

In the light detecting apparatus, the light detecting section may detect fluorescent light from the observation target that has been excited by the light emitted by the light emitting section. The light detecting apparatus may further comprise a first optical member that is arranged in an optical path of the fluorescent light from the observation target and has a transmittance for light at a peak wavelength of the fluorescent light from the observation target that is greater than a transmittance for light at a peak wavelength of the light emitted by the light emitting section. The light detecting apparatus may further comprise a second optical member that diffuses the light emitted by the light emitting section. In the light detecting apparatus, the holding section may include a heat dissipation board that releases heat generated by the light emitting section. In the light detecting apparatus, thermal conductivity of a main component of the holding section may be greater than thermal conductivity of a main component of the mount section. The light detecting apparatus may further comprise a thermal insulation member that is arranged between the holding section and the mount section, and restricts movement of heat from the holding section to the mount section. The light detecting apparatus may comprise an illumination optical system that guides the light emitted by the light emitting section to the observation target and an observation optical system that guides light from the observation target to the light detecting section, and an angle formed by an optical axis of the illumination optical system and an optical axis of the observation optical system is greater than 0° and less than or equal to 90°.

In the light detecting apparatus, the mount section may have an outer shape resulting from a second hollow pillar member connecting integrally with an outer circumference of a first hollow pillar member. In the light detecting apparatus, a cross-sectional area of the second hollow pillar member, when cleaved on a plane perpendicular to an extension direction thereof, may be less than a cross-sectional area of the first hollow pillar member, when cleaved on a plane perpendicular to an extension direction thereof. In the light detecting apparatus, an angle formed by a central axis of the first hollow pillar member and a central axis of the second hollow pillar member is greater than 0° and less than or equal to 90°. In the light detecting apparatus, an empty hole of the first hollow pillar member and an empty hole of the second hollow pillar member may be in communication inside the mount section.

In the light detecting apparatus, the mount section may have an outer shape resulting from a plurality of the second hollow pillar members connecting integrally with the outer circumference of the first hollow pillar member. In the light detecting apparatus, the empty hole of the first hollow pillar member and the empty hole of each of the plurality of second hollow pillar members may be in communication inside the mount section. In the light detecting apparatus, the light emitting section may irradiate the observation target with light via a hollow portion of the second hollow pillar member. In the light detecting apparatus, the light detecting section may receive the light from the observation target via a hollow portion of the first hollow pillar member. In the light detecting apparatus, the mount section may be secured to a surface of the test subject that includes the observation target, or at least a portion of the mount section is embedded inside the test subject.

According to a second aspect of the present invention, provided is a biometric information acquiring apparatus. The biometric information acquiring apparatus comprises the light detecting apparatus described above. The biometric information acquiring apparatus comprises a drive control section that drives the light emitting section. The biometric information acquiring apparatus comprises a data processing section that processes a detection signal generated based on the light detected by the light detecting section.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
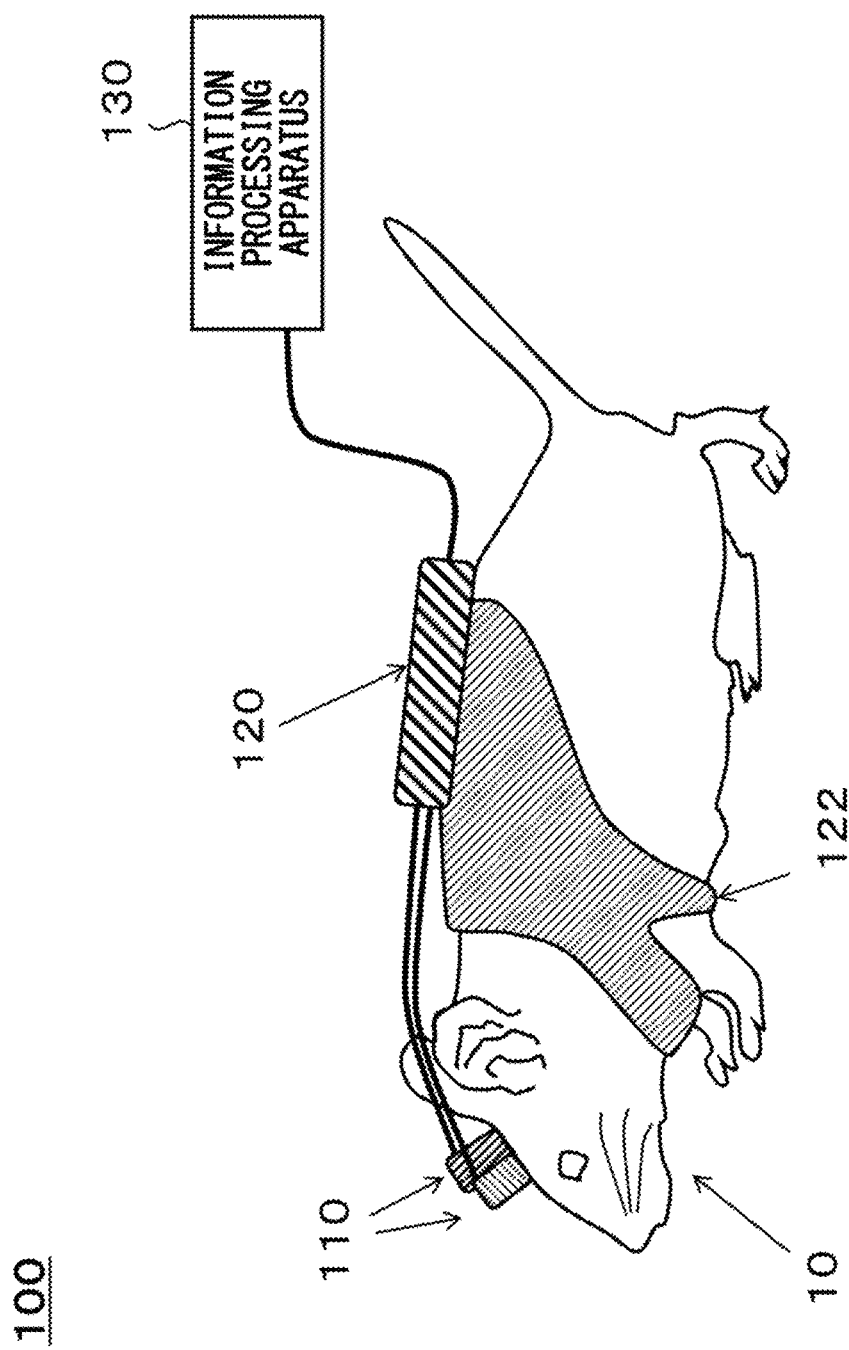
FIG. 1 schematically shows an exemplary system configuration of a biometric information gathering system 100.

FIG. 1 schematically shows an exemplary system configuration of a biometric information gathering system 100. In the present embodiment, the biometric information gathering system 100 includes an imaging apparatus 110, a relay apparatus 120, a jacket 122, and an information processing apparatus 130. In the present embodiment, the biometric information gathering system 100 is described with an example in which the imaging apparatus 110 is used to image the brain of a mouse 10. The biometric information gathering system 100 gathers information generated within living tissue during free action of the mouse 10, for example. The mouse 10 may be an example of a test subject. The brain of the mouse 10 may be an example of an observation target. The biometric information gathering system 100 may be an example of a biometric information acquiring apparatus. The imaging apparatus 110 may be an example of a light detecting apparatus.

In one embodiment, the biometric information gathering system 100 irradiates a cell of the mouse 10 with excitation light and acquires information relating to the intensity distribution of fluorescent light released from the cell, for example. When a cell of the mouse 10 is irradiated with excitation light, the cell emits fluorescent light having an intensity corresponding to the degree of activity of the cell. Therefore, information relating to the activity of the cell can be acquired by analyzing information relating to the intensity distribution of fluorescent light released from the cell. By using the information gathered by the biometric information gathering system 100, it is possible to observe or monitor, over time, processes relating to the movement or metastasis of cells emitting fluorescent light.

The biometric information gathering system 100 may stimulate a cell of the mouse 10 and observe the response to this stimulation. The method for stimulating a cell of the mouse 10 is not particularly limited, and may be electric stimulation using electrodes or optical stimulation using light with a specific wavelength. For example, the biometric information gathering system 100 irradiates a cell of the mouse 10 with stimulation light and excitation light, and acquires information relating to the intensity distribution of the fluorescent light from the cell. In this way, it is possible to observe the responses of cells to irradiation with stimulation light in real time.

In another embodiment, the biometric information gathering system 100 activates and deactivates a cell by controlling the irradiation of the cell with the stimulation light. For example, the biometric information gathering system 100 analyzes the information relating to the intensity distribution of fluorescent light from a cell of the mouse 10, and determines the irradiation conditions for the stimulation light in order to control the activity of the cell. Irradiation conditions for the stimulation light can be exemplified by the wavelength, intensity, irradiation position, irradiation timing, and the like of the stimulation light. The biometric information gathering system 100 emits the stimulation light toward the cell described above, based on the determined irradiation conditions. In this way, the activity of the cell can be controlled.

In the present embodiment, a case is described in which the observation target is a brain cell of the mouse 10. However, the observation target is not limited to a brain cell of the mouse 10. In another embodiment, the observation target may be an arbitrary cell of a plant or animal other than a human, or may be an arbitrary cell of a plant or animal including humans. The cells described above may be cells of a living organism, but do not need to be the cells of a living organism. The cells described above can be exemplified by neural cells, retinal cells, muscle cells (for example, cardiomyocytes), gland cells, and the like. Gland cells may be cells of an exocrine gland and can be exemplified by cells of the thyroid, pineal gland, digestive gland, sebaceous gland, sweat gland, and the like. The cells described above may be tissue cells that release hormones, transmitters, and the like.

In one embodiment, the cell serving as the observation target may be modified in advance through genetic manipulation to express a light-sensitive protein. Different types of genes may be expressed for each type of nerve cell by modifying genes of nerve cells using a promoter specific to the cell type. If the cell serving as the observation target is a light-sensitive cell, such as a retinal cell, gene modification of the cell does not need to be performed. Furthermore, if the observation target for fluorescent light measurement is blood flow change that is dependent on intrinsic nerve activity, flavin change in an intracellular mitochondrial metabolism system, or the like, gene modification of the cell does not need to be performed.

In another embodiment, a light-sensitive caged compound which releases a physiologically active substance due to light irradiation may be arranged in advance around the cell serving as the observation target. By using a light-sensitive protein or light-sensitive caged compound and switching the light irradiation ON/OFF, it is possible to control the excitement or excitement restriction ("excitement restriction" is sometimes referred to simply as "restriction") of an arbitrary nerve cell.

In yet another embodiment, potential-sensitive dyes, ion indicating proteins, pH indicating proteins, or the like may be introduced in advance, by performing a dyeing operation or genetic manipulation on the cell serving as the observation target. The dyeing operation can be exemplified by dyeing with ion indicators, pH indicators, or the like.

The potential-sensitive dyes can be exemplified by styryl dyes, cyanine dyes, oxonol dyes, rhodamine derivatives, or the like. When the cell into which the potential-sensitive dye has been introduced is irradiated with the excitation light, the cell emits light with an intensity corresponding to the membrane potential of the cell. The membrane potential of a cell changes according to the activity state of the cell. Therefore, information relating to the activity state of the cell can be obtained by analyzing the intensity distribution of the light released from the cell.

In the present embodiment, a case is described in which the observation target is a cell. However the observation/manipulation target is not limited to a cell. In another embodiment, the observation target or the manipulation target may be any type of tissue or biological structural element. The tissue or biological structural element described above can be exemplified by blood flow in blood vessels of a cardiovascular system, a mitochondria metabolism system of an intracellular organelle, or the like. In another embodiment, the observation target or manipulation target may be a microorganism, fungus, or the like.

According to the present embodiment, two imaging apparatuses 110 are secured to the head of the mouse 10. Furthermore, a jacket 122 with a relay apparatus 120 fitted thereto is attached to the torso of the mouse. Each of the two imaging apparatuses 110 has one end embedded in the head of the mouse 10 and can image the brain of the mouse. The other end of each of the two imaging apparatuses 110 is connected to the relay apparatus 120 via a cable. In this way, data can be transmitted from the imaging apparatuses 110 to the relay apparatus 120, and a control signal or drive power for the imaging apparatuses 110 can be provided from the relay apparatus 120 to the imaging apparatuses 110.

In the present embodiment, each imaging apparatus 110 includes an illumination optical system that irradiates the observation target with light and an observation optical system that observes the light from the observation target. For example, when a cell of the mouse 10 is irradiated with excitation light, the cell emits fluorescent light with an intensity corresponding to the degree of activity of the cell. The imaging apparatus 110 may use the illumination optical system to radiate stimulation light that stimulates a cell of the mouse 10. In this way, it is possible to activate and deactivate cells.

In the present embodiment, a case is described in which the biometric information gathering system 100 includes two imaging apparatuses 110. However, the biometric information gathering system 100 is not limited to the present embodiment. The biometric information gathering system 100 may include a single imaging apparatus 110, or may include three or more imaging apparatuses 110. Furthermore, in the present embodiment, a case is described in which a plurality of imaging apparatuses 110 are attached to the head of the mouse 10. However, the location at which the imaging apparatuses 110 are attached is not limited to the present embodiment. As an example, the plurality of imaging apparatuses 110 may be attached to the head of the mouse 10 and to the torso of the mouse 10.

In the present embodiment, the relay apparatus 120 relays at least one of information and power between the imaging apparatuses 110 and the information processing apparatus 130. For example, the relay apparatus 120 processes the data received from the imaging apparatuses 110 and generates image data. The relay apparatus 120 transmits this image data to the information processing apparatus 130. Furthermore, the relay apparatus 120 may control the imaging apparatuses 110 based on commands received from the information processing apparatus 130. The communication between the relay apparatus 120 and the information processing apparatus 130 may be wired communication, wireless communication, or a combination thereof.

The information processing apparatus 130 processes data from the imaging apparatuses 110 and stores this data. The information processing apparatus 130 includes, for example, a data processing apparatus having a processor such as a CPU, a ROM, a RAM, a communication interface, and the like; an input apparatus such as a keyboard, a pointing device, a touch panel, a microphone, or various sensors; an output apparatus such as a display apparatus or speakers; and a storage apparatus such as a memory or HDD. The information processing apparatus 130 can be exemplified by a server, a personal computer, a mobile terminal, or the like. The mobile terminal can be exemplified by a mobile telephone, a smartphone, a PDA, a tablet, a notebook computer, a laptop computer, a wearable computer, or the like.

Figure 2:
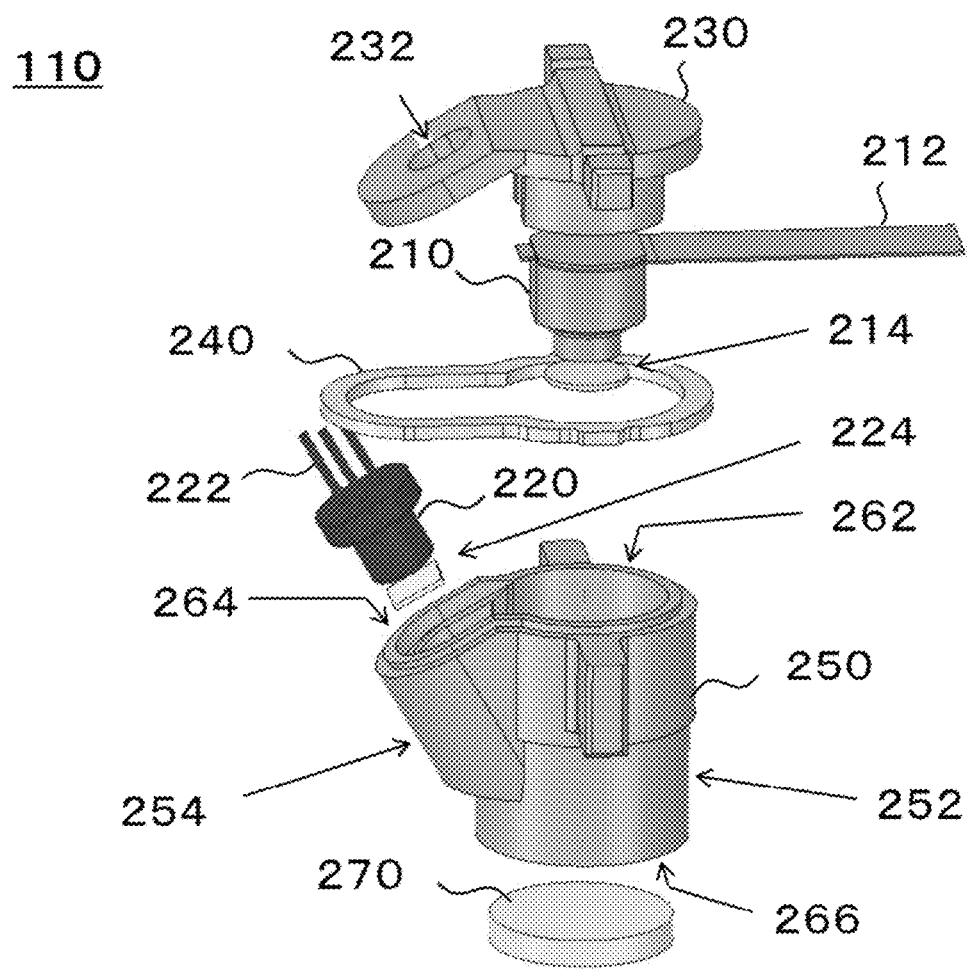
FIG. 2 schematically shows an exemplary exploded view of an imaging apparatus 110.
Figure 3:
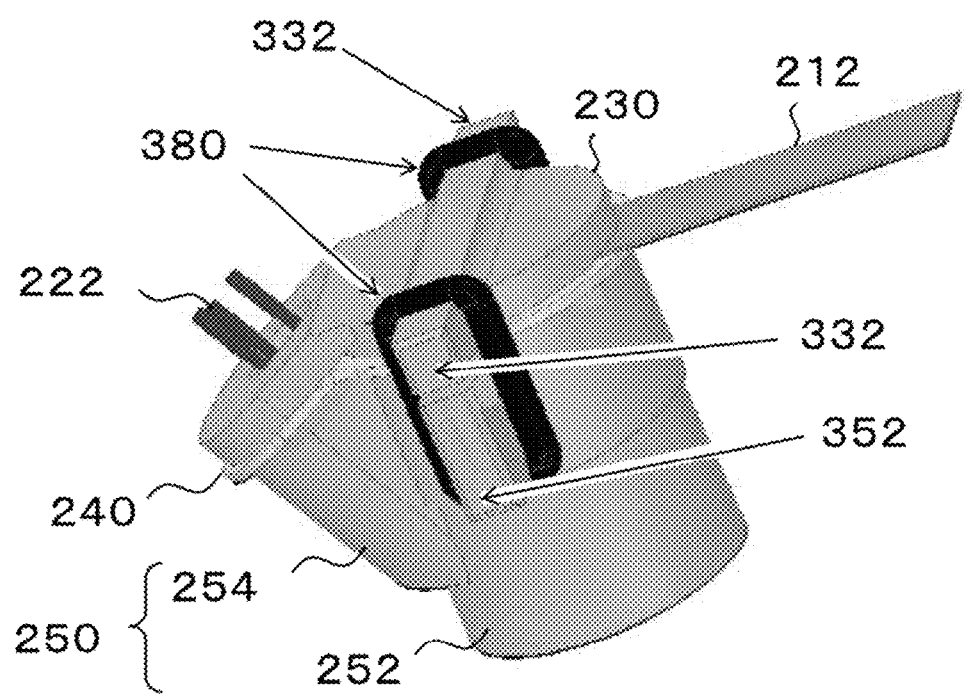
FIG. 3 schematically shows a perspective view of an imaging apparatus 110.

The imaging apparatuses 110 are described in detail using FIGS. 2 and 3. FIG. 2 schematically shows an exemplary exploded view of an imaging apparatus 110. FIG. 3 schematically shows a perspective view of an imaging apparatus 110. FIG. 3 shows a state in which a cover 230 and a mount section 250 are secured by a binding band 380.

In the present embodiment, the imaging apparatus 110 includes a camera unit 210, an optical filter 214, a light emitting unit 220, a light diffusing member 224, a cover 230, a seal member 240, a mount section 250, and an observation window 270. In the present embodiment, a cable 212 is connected to the camera unit 210 and a cable 222 is connected to the light emitting unit 220. An opening 232 is formed in the cover 230, penetrating through a portion of the cover 230. One or more protruding portions 332 are arranged on the outer edge portion of the cover 230, and one or more protruding portions 352 are arranged on the outer edge portion of the mount section 250. The mount section 250 includes a hollow member 252 and a hollow member 254. Furthermore, an opening 262, an opening 264, and an opening 266 are formed in the mount section 250.

The camera unit 210 may be an example of a light detecting section. The light emitting unit 220 may be an example of a light emitting section. The cover 230 may be an example of a holding section. The optical filter 214 may be an example of a first optical member. The light diffusing member 224 may be an example of a second optical member. The hollow member 252 may be an example of a first hollow pillar member. The hollow member 254 may be an example of a second hollow pillar member. The protruding portion 332 and the protruding portion 352 may be an example of a positioning section.

In the present embodiment, the camera unit 210 detects light from the observation target that has been irradiated with the light emitted by the light emitting unit 220. The camera unit 210 may acquire information relating to the intensity distribution of the light from the observation target. The camera unit 210 may detect the fluorescent light emitted by the observation target that has been excited by the light emitted by the light emitting unit 220. This fluorescent light may be an example of light from the observation target. The camera unit 210 may include a light receiving element such as a photodiode or an image sensor. The image sensor can be exemplified by a CMOS image sensor, a CCD image sensor, or the like.

In the present embodiment, the camera unit 210 transmits the information relating to the light from the observation target to the information processing apparatus 130, via the cable 212 and the relay apparatus 120. The camera unit 210 may operate based on commands from the relay apparatus 120 or the information processing apparatus 130. The camera unit 210 may be supplied with power from the relay apparatus 120.

In the present embodiment, the camera unit 210 is attached to one surface of the cover 230. The cable 212 may be arranged between the camera unit 210 and the one surface of the cover 230. The cable 212 may be arranged on the other surface of the cover 230.

In the present embodiment, the light from the observation target is incident to a light guiding member or a cavity arranged inside the mount section 250, via an observation window 270 arranged in the mount section 250. The observation window 270 is arranged facing the observation target of the mount section 250. Furthermore, the cavity or the light guiding member is arranged in a manner to pass through the mount section 250. After this, the light from the observation target passes through the cavity or the light guiding member described above, and arrives at the camera unit 210. If the cavity described above is formed inside the mount section 250, the camera unit 210 may be arranged inside the cavity described above.

In the present embodiment, the optical filter 214 has wavelength selectivity, and is arranged in the optical path of the light from the observation target. The optical filter 214 may be arranged on the optical axis of the camera unit 210. In the optical filter 214 according to one embodiment, the light transmittance at the peak wavelength of the fluorescent light from the observation target is greater than the light transmittance at the peak wavelength of the light emitted by the light emitting unit 220.

If the fluorescent light from the observation target is observed using the imaging apparatus 110, it is possible for the light emitted by the light emitting unit 220 to be reflected inside the mount section 250, the observation window 270, the cell of the mouse 10, and the like to arrive at the camera unit 210. As described above, the light of the light emitting unit 220 interferes with the observation of fluorescent light, but it is possible to accurately observe the fluorescent light from the observation target by arranging the optical filter 214 in the optical path of the light from the observation target.

In the present embodiment, the light emitting unit 220 emits light. The light emitting unit 220 may adjust at least one of the wavelength, intensity, irradiation position, and irradiation timing of the light being emitted, based on commands from the relay apparatus 120 and the information processing apparatus 130.

The light emitting unit 220 may include a light source such as a laser diode, LED, or organic EL. The light emitting unit 220 may include one or more light sources. The light emitting unit 220 may include a plurality of light sources with different peak wavelengths. For example, the light emitting unit 220 includes a light source for excitation light and a light source for stimulation light. The light emitting unit 220 may include one or more light sources for excitation light corresponding respectively to a plurality of elements in the observation target, and may include one or more light sources for stimulation light corresponding respectively to a plurality of elements in the observation target.

The light source may be a laser diode. The laser diode may be a packaged laser diode, or may be a laser diode bare chip. If a laser diode is used as the light source, it is possible to make the intensity of the light from the observation target greater than in a case where an LED or organic EL is used as the light source. Therefore, a miniature camera unit can be used. Furthermore, the SN ratio can be improved. As a result, it is possible to provide a miniature imaging apparatus that is particularly suitable for fluorescent light imaging, for example.

In the present embodiment, the light emitting unit 220 is attached to one surface of the cover 230, in a manner to cover the opening 232 of the cover 230. In this way, the other end of the cable 222 that has one end connected to the light emitting unit 220 can be lead through the opening 232 to the other surface side of the cover 230. Furthermore, dust, liquid, and the like can be restricted from entering into the mount section 250 from the opening 232.

In the present embodiment, the light emitted by the light emitting unit 220 (sometimes referred to as the light from the light emitting unit 220) passes through the cavity or light guiding member arranged inside the mount section 250, to be emitted from the observation window 270. After this, the light reaches the observation target and irradiates the observation target. If the cavity described above is formed inside the mount section 250, the light emitting unit 220 may be arranged inside the cavity described above.

In the present embodiment, the light diffusing member 224 diffuses the light emitted by the light emitting unit 220. In this way, irradiation unevenness is restricted and a wide range of the observation target can be irradiated with light. In the present embodiment, the light diffusing member 224 is arranged in the optical path of the light emitted by the light emitting unit 220. The light diffusing member 224 may be arranged on the optical axis of the light emitting unit 220. The light diffusing member 224 can be exemplified by an LSD (Light Shaping Diffuser).

In the present embodiment, the cover 230 is attached to the mount section 250 in a freely detachable manner. The cover 230 is attached to the mount section 250 in a manner to cover the opening 262 and the opening 264 of the mount section 250, for example. In this way, dust, liquid, and the like are restricted from entering into the mount section 250 from the opening 262 and the opening 264. The opening 262 and the opening 264 may be linked, and may form a single opening. The opening 262 and the opening 264 may be formed in the same plane, or may be formed in different planes.

In the present embodiment, one or more protruding portions 332 are arranged on the outer edge portion of the cover 230, and each of the one or more protruding portions 332 is linked to a corresponding protruding portion 352 among one or more protruding portions 352 arranged on the mount section 250. The method for linking the protruding portion 332 and the protruding portion 352 is not particularly limited. The protruding portion 332 and the protruding portion 352 may be linked using a binding member such as a binding band 380, or may be linked by interlocking. Other examples of the linking method for the cover 230 and the mount section 250 can include fastening with a screw, securing with a clip, reattachable bonding, and the like. In this way, when the cover 230 is attached to the mount section 250, it is possible to position the cover 230 relative to the mount section 250. As a result, the relative positional relationship between the cover 230 and the mount section 250 can be set.

In the present embodiment, the cover 230 holds the camera unit 210 and the light emitting unit 220. The cover 230 holds the camera unit 210 and the light emitting unit 220 such that the relative positional relationship between the camera unit 210 and the light emitting unit 220 is fixed, for example. The relative positional relationship between the camera unit 210 and the light emitting unit 220 may be determined such that the reflected light, which is from the light emitting unit 220 and reflected inside the light guiding member or the cavity of the mount section 250, does not directly reach the camera unit 210.

In this way, by attaching the camera unit 210 and the light emitting unit 220 to the cover 230, it is possible to fix the position and direction of the light emission by the light emitting unit 220 and the position and direction of the light reception by the camera unit 210. Therefore, with the present embodiment, the observation target, the camera unit 210, and the light emitting unit 220 can be positioned with good reproducibility. As a result, highly accurate data can be acquired with little variation.

For example, a cover 230 is prepared having a plurality of mount sections 250, a camera unit 210, and a light emitting unit 220 attached thereto. Furthermore, in addition to the cover 230 having the camera unit 210 and the light emitting unit 220 attached thereto, a plurality of second covers corresponding respectively to the plurality of mount sections 250 are prepared. The structures and materials of the second covers are not particularly limited, as long as these second covers can cover the opening 262 and the opening 264. For example, the second covers have the same shape as the cover 230, except that the opening 232 is not formed therein.

Next, the plurality of mount sections 250 are attached respectively to a plurality of mice, and then rearing of the plurality of mice is started. At this time, a second cover is attached to each of the plurality of mount sections 250. After this, at a suitable time, the cover 230 having the second camera unit 210 and the light emitting unit 220 attached thereto is used to observe the brains of the plurality of mice in order. More specifically, first, the second cover is removed from the mount section 250 of the mouse that is to be the test subject, and the cover 230 having the camera unit 210 and the light emitting unit 220 attached thereto is attached to this mount section 250. Next, the imaging apparatus 110 is manipulated via the information processing apparatus 130 to observe the state of the brain of the mouse 10.

With the present embodiment, the operation described above is applied to each of the plurality of mice, thereby making it possible to use the same camera unit 210 and light emitting unit 220 to easily observe the brains of the plurality of mice. As a result, highly accurate data can be acquired with little variation. In another embodiment, covers 230 are prepared corresponding respectively to the plurality of mount sections 250, and the brains of the plurality of mice may be observed simultaneously.

The cover 230 may restrict heat transfer from the light emitting unit 220 to the observation target. In this way, it is possible to restrict death or alteration of the observation target, for example. With one embodiment, the cover 230 includes a heat dissipation member that releases the heat generated by the light emitting unit 220. The heat dissipation member can be exemplified by a metal heat sink. The cover 230 may function as a heat sink.

With another embodiment, the material of the main component of the cover 230 is determined such that the thermal conductivity of the main component of the cover 230 greater than the thermal conductivity of the main component of the mount section 250. The main component may be a component that occupies more than 50% of at least one of the weight, volume, and surface area. The thermal conductivity of the material of the portion of the cover 230 in contact with the mount section 250 may be determined to be greater than the thermal conductivity of the material of the portion of the mount section 250 in contact with the cover 230.

In yet another embodiment, a thermal insulation material with lower thermal conductivity than the material of the main component of the cover 230 may be arranged between at least portions of the cover 230 and mount section 250. In this way, the overall heat transfer coefficient between the cover 230 and the mount section 250 can be reduced. As a result, the transfer of the heat generated by the light emitting unit 220 to the mount section 250 is restricted.

In the present embodiment, the seal member 240 is arranged between the cover 230 and the mount section 250, and seals the gap between the cover 230 and the mount section 250. In this way, dirt, liquid, and the like can be restricted from entering into the mount section 250. The seal member 240 may be shaped as a ring that matches the outer circumferential shape of the opening 262 and opening 264. The seal member 240 may include a material with a lower thermal conductivity than the main component of the cover 230. In this way, the heat generated by the light emitting unit 220 can be restricted from being transferred to the mount section 250 via the cover 230.

In the present embodiment, the mount section 250 includes a thermal insulation member at an end portion on the side facing the cover 230. The thermal insulation member is arranged at a portion where the cover 230 contacts the mount section 250, and restricts the movement of heat from the cover 230 to the mount section 250. The thermal conductivity of the thermal insulation member is less than the thermal conductivity of the main component of the cover 230, for example. The thermal insulation member may be a material with low thermal conductivity such as rubber, ceramic, or a porous body. The thermal insulation member may include a transparent thermal insulation material such as aerosol.

In the present embodiment, the mount section 250 is attached to the mouse 10. In one embodiment, the mount section 250 may be secured to the surface of the mouse 10, or at least a portion of the mount section 250 may be embedded inside the mouse 10. If a portion of the mount section 250 is embedded in the body of the mouse 10, the length of the portion embedded in the body of the mouse 10 may be less than or equal to 1 cm, is preferably less than or equal to 5 mm, is more preferably less than or equal to 3 mm, and is even more preferably less than or equal to 1 mm. In this way, it is possible to restrict the invasiveness.

In another embodiment, the mount section 250 may be invasively implanted. At this time, a portion of the tissue on the surface of the test subject may be removed. In this way, a stepped portion is formed on the surface of the test subject, and it is possible to perform implantation with low invasiveness. For example, if the mount section 250 is being implanted in the brain of the mouse 10, the cerebral cortex that is the surface layer of the brain may be removed, and then one end of the mount section 250 may be inserted at this location.

In the present embodiment, the observation window 270 is arranged on the surface of the mount section 250 facing the observation target. The observation window 270 prevents dust, liquid, and the like from entering into the mount section 250. The observation window 270 may be transparent with respect to the light emitted by the light emitting unit 220. The observation window 270 may be formed by a material for which the transmittance at the peak wavelength of the light emitted by the light emitting unit 220 is greater than or equal to 80%, a material for which this transmittance is greater than or equal to 85%, a material for which this transmittance is greater than or equal to 90%, a material for which this transmittance is greater than or equal to 95%, or a material for which this transmittance exceeds 98%.

The observation window 270 may be transparent with respect to the light from the observation target. The observation window 270 may be formed by a material for which the transmittance at the peak wavelength of the light from the observation target is greater than or equal to 80%, a material for which this transmittance is greater than or equal to 85%, a material for which this transmittance is greater than or equal to 90%, a material for which this transmittance is greater than or equal to 95%, or a material for which this transmittance exceeds 98%.

In the present embodiment, an example of the imaging apparatus 110 is described in which a single camera unit 210 and a single light emitting unit 220 are attached to the cover 230. However, the imaging apparatus 110 is not limited to the present embodiment. In another embodiment, a plurality of camera units 210 may be attached to the cover 230. Furthermore, a plurality of light emitting units 220 may be attached to the cover 230.

In the present embodiment, an example of the imaging apparatus 110 is described in which the light emitting unit 220 illuminates the observation target through the light diffusing member 224. However, the imaging apparatus 110 is not limited to the present embodiment. In another embodiment, if the light emitting unit 220 has suitable light distribution, the imaging apparatus 110 does not need to include the light diffusing member 224. In the present embodiment, an example of the imaging apparatus 110 is described in which the camera unit 210 detects the light from the observation target via the optical filter 214. However, the imaging apparatus 110 is not limited to the present embodiment. In another embodiment, the imaging apparatus 110 does not need to include the optical filter 214.

Figure 4:
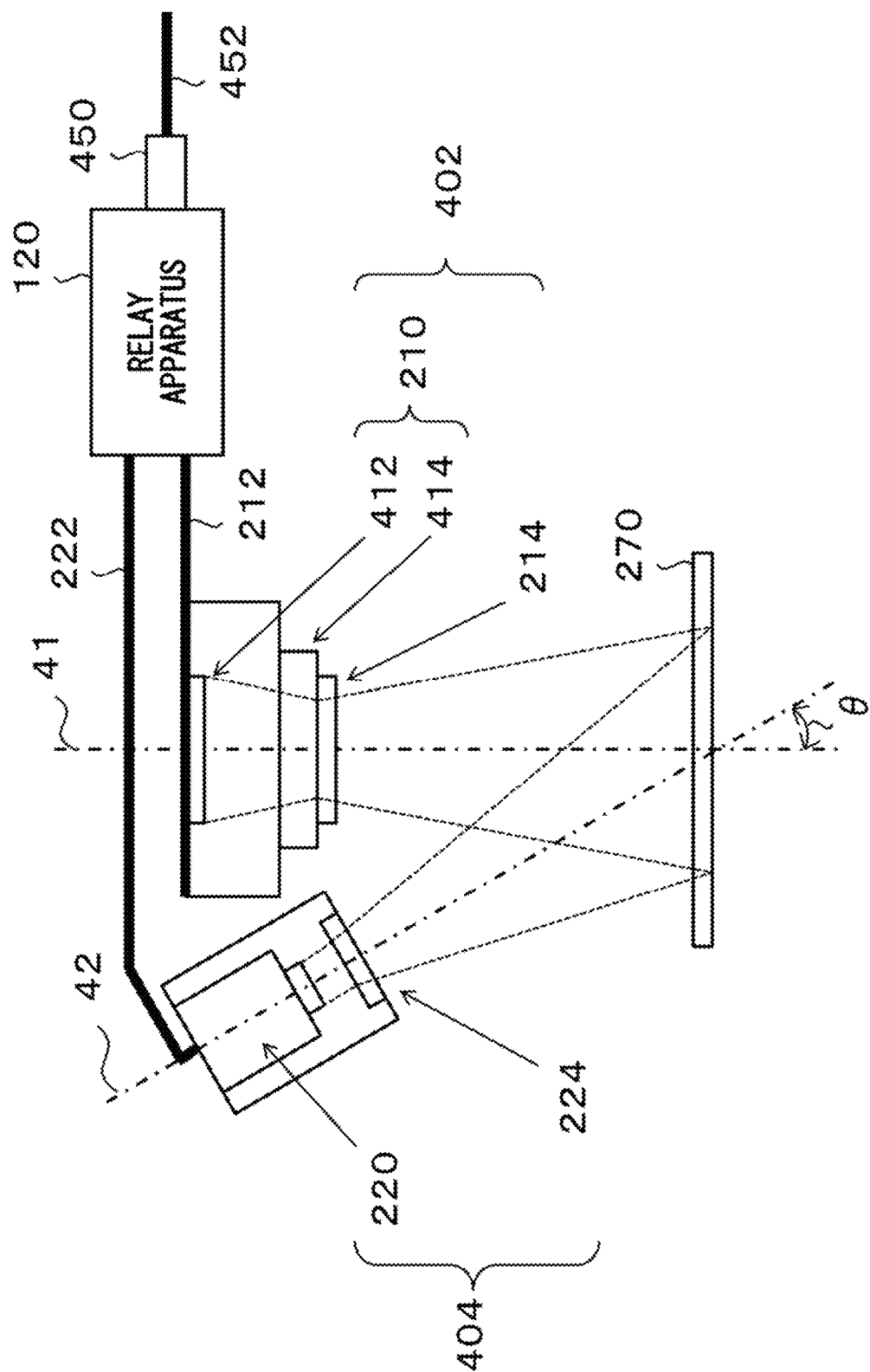
FIG. 4 schematically shows an exemplary system configuration of the imaging apparatus 110.

FIG. 4 schematically shows an exemplary system configuration of the imaging apparatus 110. In the present embodiment, an observation optical system 402 includes the camera unit 210 and the optical filter 214. The camera unit 210 includes an image sensor 412 and a lens unit 414. Furthermore, the illumination optical system 404 includes the light emitting unit 220 and the light diffusing member 224.

The observation optical system 402 only needs to guide the light from the observation target to the camera unit 210, and the configuration thereof is not particularly limited. The observation optical system 402 may include arbitrary optical members such as a lens, a filter, optical fiber, an optical waveguide, a mirror, a prism, and an optical path length adjusting member. The illumination optical system 404 only needs to guide the light emitted by the light emitting unit 220 to the observation target, and the configuration thereof is not particularly limited. The illumination optical system 404 may include arbitrary optical members such as a lens, a filter, optical fiber, an optical waveguide, a mirror, a prism, an optical path length adjusting member, and a light diffusion board.

The angle θ formed by the optical axis 41 of the observation optical system 402 and the optical axis 42 of the illumination optical system 404 may be greater than 0° and less than or equal to 90°. The angle θ is determined in consideration of ensuring luminance uniformity of the irradiation region and restricting regular reflection components from being incident within the angle of field of the observation optical system, for example. The smaller the angle θ, the more efficient the irradiation light and the illumination region uniformity. Furthermore, it is possible to miniaturize the imaging apparatus 110. On the other hand, the larger the angle θ, the more difficult it is for regular reflected light to be incident within the angle of field of the observation optical system, and it is possible to increase the angle of field of the imaging.

The angle θ may be determined in consideration of the length of the mount section 250 in the direction of the optical axis of the observation optical system. The greater the length of the mount section 250 in the direction of the optical axis of the observation optical system, the smaller the imaging angle of field. Therefore, the value of the angle θ desired to restrict the regular reflected light from being incident within the angle of field of the observation optical system becomes small, while preserving the luminance uniformity of the observation target. On the other hand, the shorter this length of the mount section 250 described above, the larger the imaging angle of field. Therefore, the value of the angle θ desired to restrict the regular reflected light from being incident within the angle of field of the observation optical system becomes large, while preserving the luminance uniformity of the observation target.

The angle θ is preferably greater than or equal to 10° and less than or equal to 60°, more preferably greater than or equal to 15° and less than or equal to 45°, and even more preferably greater than or equal to 20° and less than or equal to 40°. With one embodiment, the angle θ is greater than or equal to 25° and less than or equal to 35°. The angle θ may be 30°. In this way, it is possible to restrict the regular reflected light from being incident within the angle of field of the observation optical system, while preserving the luminance uniformity of the observation target. Furthermore, it is possible to illuminate the observation target with light from diagonally above or from a horizontal direction. Therefore, the imaging apparatus 110 can be simplified in comparison to a case where coaxial vertical illumination is used. As a result, the imaging apparatus 110 can be made smaller and lighter weight.

In the present embodiment, the relay apparatus 120 is connected to a cable 452 via an overload prevention member 450. The overload prevention member 450 can be exemplified by an extending member such as a reel including a spring, rubber, or a stopper, or an attachable/detachable connecting member such as a magnetic cable connecting member. In this way, when the cable 452 is pulled for whatever reason, it is possible to prevent damage to at least one of the mouse 10, the camera unit 210, and the light emitting unit 220.

Figure 5:
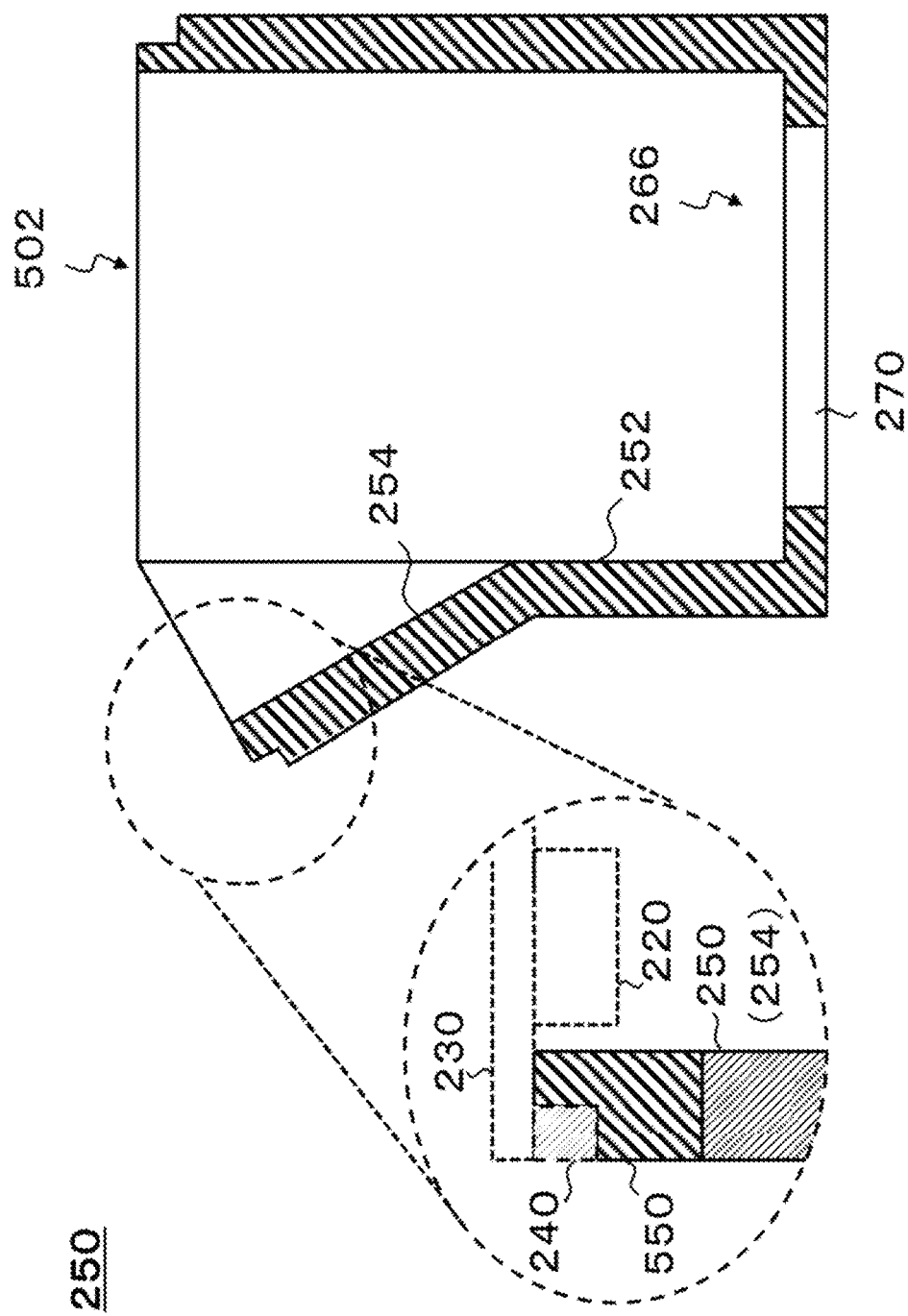
FIG. 5 schematically shows an exemplary cross-sectional view of the mount section 250.

FIG. 5 schematically shows an exemplary cross-sectional view of the mount section 250. The portion of FIG. 5 encircled with a dotted line is a partial magnified view of the connection portion between the cover 230 and the mount section 250, in a state where the cover 230 is attached to the mount section 250. In the present embodiment, the mount section 250 has an outer shape in which the hollow member 254 is integrally joined with the outer circumference of the hollow member 252. The hollow member 252 and the hollow member 254 are shaped as hollow pillars. For example, the camera unit 210 receives the light from the observation target via the empty hole of the hollow member 252. The light emitting unit 220 irradiates the observation target with light via the empty hole of the hollow member 254. The angle formed by the central axis of the hollow member 252 and the central axis of the hollow member 254 may be greater than 0° and less than or equal to 90°.

The hollow member 252 and the hollow member 254 may have a light shielding property. In this way, it is possible to reduce the intensity of the outside light that is incident to the inside of the mount section 250. The inner surfaces of the hollow member 252 and the hollow member 254 may be coated with a light absorbing material that absorbs the light emitted by the light emitting unit 220. By absorbing the reflected light inside the mount section 250 with the light absorbing material, it is possible to reduce the noise caused by this reflected light.

The cross-sectional area of the hollow member 254, when the hollow member 254 is cleaved along a plane perpendicular to the extension direction thereof, may be less than the cross-sectional area of the hollow member 252 when the hollow member 252 is cleaved along a plane perpendicular to the extension direction thereof. The shapes of the cross sections of the hollow member 252 and the hollow member 254 when cleaved in a plane perpendicular to the extension direction are not particularly limited. The shapes of these cross sections may be circular, elliptical, polygonal, or a more complicated shape.

In the present embodiment, the empty hole of the hollow member 252 and the empty hole of the hollow member 254 are in communication within the mount section 250, and form the cavity 502 as a single body. The empty hole of the hollow member 252 and the empty hole of the hollow member 254 may be in uninterrupted communication with each other within the mount section 250. In this way, it is possible to effectively utilize the space inside the cavity 502. As a result, it is possible to further miniaturize the imaging apparatus 110. For example, if the cover 230 is attached to the mount section 250, at least one of the camera unit 210 and the light emitting unit 220 can be housed inside the cavity 502. The light emitting unit 220 may be configured to be housed inside the empty hole of the hollow member 254.

Furthermore, an optical member for changing the progression direction of the light emitted by the light emitting unit 220 is preferably not arranged in the cavity 502 inside the mount section 250. This optical member can be exemplified by a mirror, a prism, or the like. In this way, it is possible to simplify the structure of the imaging apparatus 110. As a result, the imaging apparatus 110 can be further miniaturized and made lighter weight.

As an embodiment example, a mount section 250 was manufactured in which an optical member was not arranged inside the cavity 502 and, when the cover 230 was attached to the mount section 250, the camera unit 210 and the light emitting unit 220 were housed inside the cavity 502. In this way, even when a packaged laser diode was used as the light emitting unit 220, it was possible to manufacture an imaging apparatus 110 with outer dimensions of less than 10 mm×less than 10 mm×less than 10 mm and a mass of less than 1 g. Furthermore, it was possible to form an extremely lightweight imaging system in which the total mass of the imaging apparatus 110 and the relay apparatus 120 was approximately 0.9 g. With this imaging system, it was possible to capture images of an extremely large area with dimensions of 4 mm×5.3 mm.

As described above, with the present embodiment, the imaging system is extremely lightweight, so that even for a mouse whose weight is approximately from 25 g to 35 g, it is possible to attach three or four of the imaging apparatuses 110 and attach a plurality of camera units 210 to the cover 230. Furthermore, since the imaging apparatus 110 is extremely small, it is also possible to attach a plurality of imaging apparatuses 110 to the head of the mouse. In this way, it is possible to capture almost all of the cerebral cortex of a mouse with a single instance of imaging.

A conventional miniature imaging system has a problem that the imaging area is small (up to approximately 900 μm×650 μm, as shown in Non-Patent Document 9, for example). However, by using the imaging apparatus 110 according to the present embodiment, it is possible to provide an imaging system that is smaller and more lightweight than a conventional imaging system and can also capture an image of a wide area while maintaining enough resolution to distinguish cells.

In the present embodiment, the mount section 250 includes a thermal insulation member 550 on the end portion of the side facing the cover 230. By arranging the thermal insulation member 550 at a portion where the cover 230 and the mount section 250 are in contact, it is possible to restrict the movement of heat from the cover 230 to the mount section 250, which is from the holding section to the mount section. The thermal insulation member 550 may be a material with low thermal conductivity, such as rubber or ceramic. The thermal insulation member 550 may include a transparent thermal insulation material such as aerosol.

If the thermal insulation member 550 is arranged on the end portion of the mount section 250, the thermal insulation member 550 may include a concave portion in which the seal member 240 is to be arranged, on the outer edge portion of the end portion on the side facing the cover 230. In the present embodiment, an example of the thermal insulation member 550 is described in which the thermal insulation member 550 is arranged on the end portion of the mount section 250. However, the thermal insulation member 550 is not limited to the present embodiment.

In another embodiment, the thermal insulation member 550 may (i) be arranged on a portion of the mount section 250, (ii) be arranged on a portion of the cover 230, or (iii) be a material that is separate from the mount section 250 and the cover 230 and arranged between the mount section 250 and the cover 230. In one embodiment, the thermal insulation member 550 may be formed integrally with the seal member 240. In another embodiment, the thermal insulation member 550 may be arranged in a middle portion of the mount section 250, or may be arranged in the end portion of the mount section 250 on the observation target side that is in contact with the observation target.

In the present embodiment, an example of the mount section 250 is described in which the mount section 250 has an outer shape obtained by forming a single hollow member 254 integrally on the outer circumference of the hollow member 252. However, the mount section 250 is not limited to the present embodiment. In another embodiment, the mount section 250 may have an outer shape obtained by connecting a plurality of hollow members 254 integrally to the outer circumference of the hollow member 252. In this case as well, the empty hole of the hollow member 252 and each of the empty holes of the plurality of hollow members 254 may be in communication with each other inside the mount section 250.

Furthermore, an opening for inserting a tool into the cavity from outside the mount section 250 may be formed in the mount section 250. In addition, this opening may be provided with an attachable lid to restrict dust, liquid, and the like from entering into the mount section 250. The plurality of hollow members described above may be an example of openings for inserting tools. An access path to the observation target can be ensured. The tools can be exemplified by a pipette, a capillary, a microtube, an electrode needle, a sampling needle, and the like.

Figure 6:
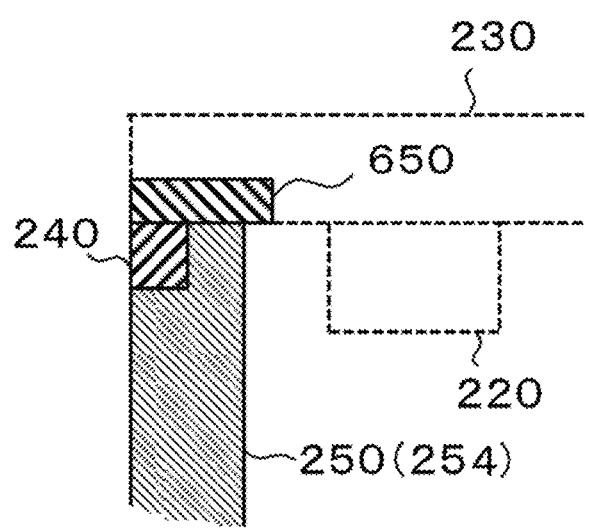
FIG. 6 schematically shows an exemplary thermal insulation member 650.

FIG. 6 schematically shows an exemplary thermal insulation member 650. FIG. 6 is a partial magnified view of a connection portion between the cover 230 and the mount section 250, in a state where the cover 230 is attached to the mount section 250. In the embodiment described in relation to FIG. 5, the thermal insulation member 550 is described as being arranged at an end portion of the mount section 250. The present embodiment differs from the embodiment described in relation to FIG. 5 in that the thermal insulation member 650 is arranged on the cover 230. Aside from this difference, the present embodiment may have the same configuration as the embodiment described in relation to FIG. 5. The structure, material, and the like of the thermal insulation member 650 may be the same as those of the thermal insulation member 550.

Figure 7:
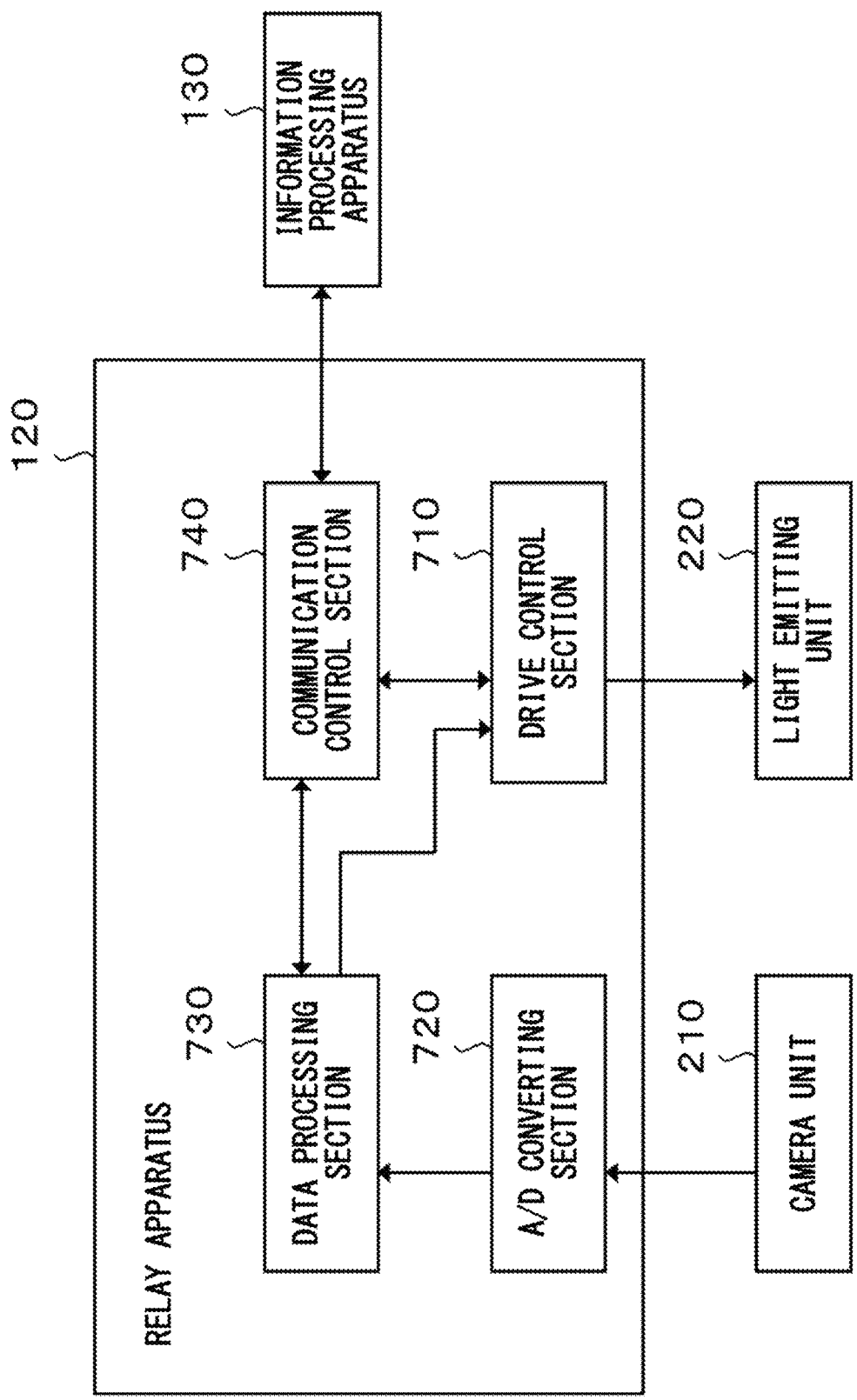
FIG. 7 schematically shows an exemplary system configuration of the relay apparatus 120.

FIG. 7 schematically shows an exemplary system configuration of the relay apparatus 120. In the present embodiment, the relay apparatus 120 includes a drive control section 710, an A/D converting section 720, a data processing section 730, and a communication control section 740.

The drive control section 710 controls the driving of the light emitting unit 220. For example, the drive control section 710 controls the driving of the light emitting unit 220 based on commands from the information processing apparatus 130. The drive control section 710 controls the wavelength, intensity, irradiation position, irradiation timing, and the like of the light emitted by the light emitting unit 220, for example. The A/D converting section 720 converts an analog detection signal, which is generated by a photoelectric conversion in the camera unit 210, into digital data. If the camera unit 210 outputs a digital signal, the relay apparatus 120 does not need to include the A/D converting section 720, and the output of the camera unit 210 may be input directly into the data processing section 730.

In one embodiment, the data processing section 730 processes the digital data received from the A/D converting section 720 to generate image data. The data processing section 730 may transmit the image data to the information processing apparatus 130 via the communication control section 740.

In another embodiment, the data processing section 730 analyzes the digital data received from the A/D converting section 720 and determines the irradiation conditions for the stimulation light and the excitation light, in order to control the activity of a cell that is the observation target or manipulation target. The irradiation conditions for the stimulation light can be exemplified by the wavelength, intensity, irradiation position, irradiation timing, and the like of the stimulation light. For example, first, the data processing section 730 determines the wavelength of the stimulation light in order to control the activity of the cell that is the observation target or manipulation target. Next, the wavelength of the excitation light is determined such that the stimulation light, the excitation light, and fluorescent light have different wavelengths.

The communication control section 740 controls communication with the information processing apparatus 130. The communication control section 740 may be a variety of communication interfaces. The communication control section 740 may correspond to a plurality of communication methods. The communication control section 740 may control wireless communication with the information processing apparatus 130. The communication control section 740 may transmit commands from the information processing apparatus 130 to the drive control section 710 or the data processing section 730.

Figure 8:
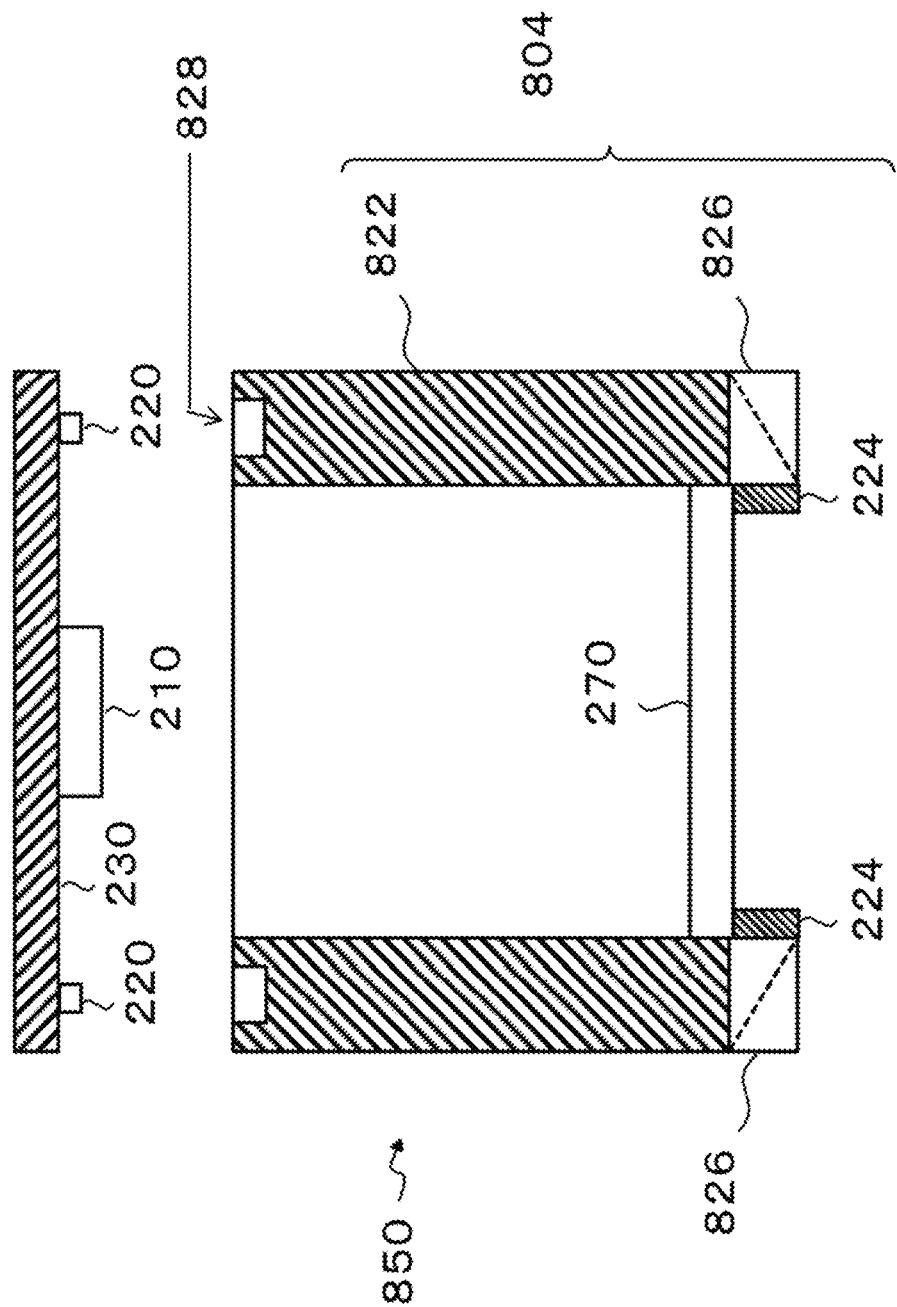
FIG. 8 schematically shows an exemplary cross-sectional view of an imaging apparatus 810.

FIG. 8 schematically shows an exemplary cross-sectional view of an imaging apparatus 810. In the present embodiment, the imaging apparatus 810 includes the camera unit 210, one or more light emitting units 220, the cover 230, a mount section 850, and the observation window 270. In the present embodiment, the imaging apparatus 810 differs from the imaging apparatus 110 by including an illumination optical system 804. The illumination optical system 804 includes a light guiding member 822, a mirror member 826, and the light diffusing member 224. The light emitting unit 220 may be a laser diode bare chip. The mirror member 826 may be a prism.

The following describes the main differences between the imaging apparatus 810 and the imaging apparatus 110. Features other than these differences may be the same in the imaging apparatus 810 as in the imaging apparatus 110. Furthermore, in order to simplify the description, FIG. 8 focuses on only the main components of the imaging apparatus 810. For example, the imaging apparatus 810 includes the seal member 240 that is not shown, between the cover 230 and the mount section 850.

In the present embodiment, the body of the mount section 850 is formed by a hollow pillar member, and this hollow pillar member is used as the light guiding member 822 of the illumination optical system 804. Furthermore, a concave portion 828 for housing the light emitting unit 220 is formed on the end portion of the light guiding member 822 on the side facing the cover 230. The position and size of the concave portion 828 may be determined such that the light emitting unit 220 does not contact the light guiding member 822 when the cover 230 is attached to the mount section 850. In this way, it is possible to restrict the transfer of heat from the light emitting unit 220 to the light guiding member 822.

With the present embodiment, the light emitted by the light emitting unit 220 is incident to the light guiding member 822 from the bottom surface of the concave portion 828 formed in the light guiding member 822. The light incident to the light guiding member 822 passes through the inside of the light guiding member 822, and is then reflected by the mirror member 826 to reach the observation target via the light diffusing member 224. The mirror member 826 only needs to be an optical element that can change the angle of light, and the structure, type, reflection angle, and the like of the mirror member 826 are not particularly limited. With the present embodiment, it is possible to radiate light from the horizontal direction of the observation target. In this way, it is possible to efficiently observe the fluorescent light from the observation target.

For example, if the observation target is a strong scattering body, the imaging apparatus 810 may omit at least one of the mirror member 826 and the light diffusing member 224. Furthermore, the mirror member 826 is housed in the light guiding member 822, and the illumination optical system 804 may include a surface that is flat relative to the observation target.

Figure 9:
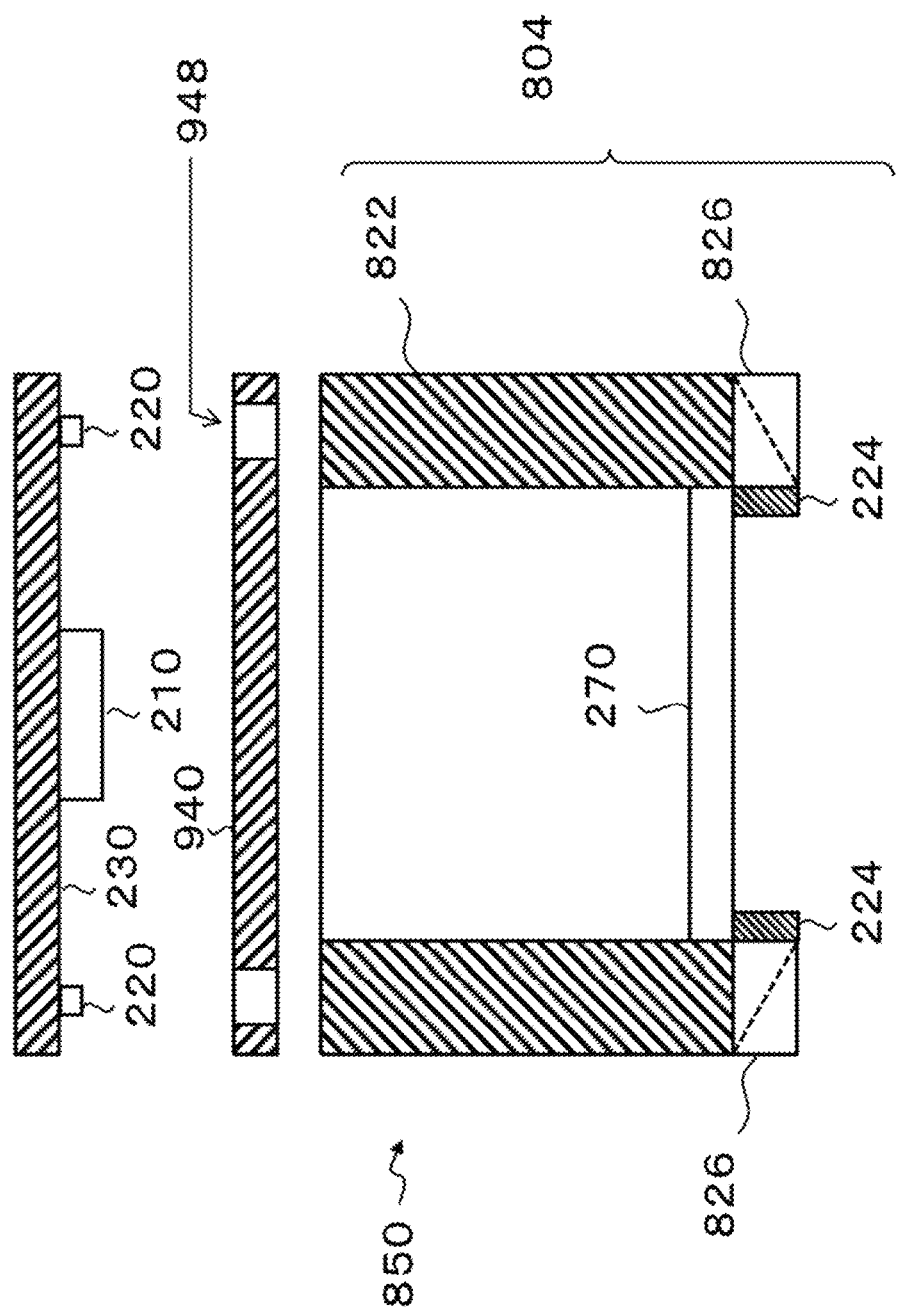
FIG. 9 schematically shows an exemplary cross-sectional view of an imaging apparatus 910.

FIG. 9 schematically shows an exemplary cross-sectional view of an imaging apparatus 910. In the present embodiment, the imaging apparatus 910 includes the camera unit 210, one or more light emitting units 220, the cover 230, a seal member 940, the mount section 850, and the observation window 270. The imaging apparatus 910 may have the same configuration as the imaging apparatus 810, except that the seal member arranged between the cover 230 and the mount section 850 includes a through-hole 948 and the concave portion 828 is not formed in the light guiding member 822.

In the present embodiment, the position and size of the through-hole 948 are designed to enable housing of the light emitting unit 220 when the cover 230 is attached to the mount section 850. Furthermore, the thickness of the seal member 940 is designed such that the tip of the light emitting unit 220 (e.g. the emission surface) does not contact the light guiding member 822 when the cover 230 is attached to the mount section 850. In this way, it is possible to restrict the transfer of heat from the light emitting unit 220 to the mount section 850.

In the present embodiment, a case is described in which a through-hole 948 is formed in the seal member 940. However, the seal member 940 is not limited to the present embodiment. In another embodiment, a concave portion may be formed in the seal member 940 instead of the through-hole 948. This concave portion may be designed such that the tip of the light emitting unit 220 does not contact the concave portion when the cover 230 is attached to the mount section 850. If the seal member 940 is formed of a transparent thermal insulation material, the seal member 940 may be designed such that the emission surface of the light emitting unit 220 contacts the bottom surface of the concave portion. In this way, the irradiation efficiency can be improved.

(Illumination Method of the Imaging Apparatus)

As shown above using FIGS. 1 to 9, the imaging apparatus 110, the imaging apparatus 810, and the imaging apparatus 910 that are examples of light detecting apparatuses are described in detail. As shown in FIGS. 4, 8, and 9, in the imaging apparatus 110, the imaging apparatus 810, and the imaging apparatus 910, a side illumination method, and not a coaxial vertical illumination, is used as the illumination method.

If a coaxial vertical illumination is used as the illumination method of the imaging apparatus, an optical member for changing the progression direction of the light emitted by the light emitting unit 220 is arranged in the cavity inside the mount section. The optical member for changing the progression direction of the light emitted by the light emitting unit 220 is exemplified by a half mirror, a beam splitter, a dichroic mirror, a dichroic prism, or the like. Furthermore, an optical member for converting the light emitted by the light emitting unit 220 into parallel light is necessary. The optical member for converting the light emitted by the light emitting unit 220 into parallel light is exemplified by a collimator or the like. Therefore, if a coaxial vertical illumination method is adopted as the illumination method of the imaging apparatus, it is difficult to reduce the dimensions and mass of the imaging apparatus.

In contrast to this, if a side illumination method is adopted as the illumination method of the imaging apparatus, there is no need to arrange an optical member for changing the progression direction of the light emitted by the light emitting unit 220 in the cavity inside the mount section. Furthermore, there is no need for an optical member for converting the light emitted by the light emitting unit 220 into parallel light. Therefore, if a side illumination method is adopted as the illumination method of the imaging apparatus, the structure of the imaging apparatus is much simpler than in a case where a coaxial vertical illumination method is adopted. As a result, the imaging apparatus can be made smaller and lighter weight.

As an example, if the imaging apparatus 110, the imaging apparatus 810, or the imaging apparatus 910 is used to acquire biometric information of a small animal, the mass of each imaging apparatus may be less than 5 g or less than 4 g, preferably less than 3 g. Furthermore, the mass of each imaging apparatus is more preferably less than 2 g, and even more preferably less than 1 g. The small animal is exemplified by a rodent.

If the imaging apparatus 110, the imaging apparatus 810, or the imaging apparatus 910 is used to acquire biometric information of a test animal, the mass of each imaging apparatus may be less than or equal to ⅕ the weight of the test animal, preferably less than or equal to ¹⁄₁₀ the weight of the test animal, more preferably less than or equal to ¹⁄₁₅ the weight of the test animal, and even more preferably less than or equal to ¹⁄₂₀ the weight of the test animal. For example, even if a rodent has an object with a mass of approximately ¹⁄₁₀ of its own weight attached thereto, no significant change is seen in the behavior of the rodent.

The inventors of the present invention verified the relationship between the total mass of the imaging apparatus attached to a mouse and the behavioral state of the mouse, using a C57/B6 strain of mouse. The results showed that, when the total mass of the imaging apparatus attached to a mouse was 10% of the weight of the mouse, the mouse exhibited the same behavioral state as in a case where the imaging apparatus is not attached. Specifically, there was no significant fluctuation in an exercise capability evaluation score of a specific task.

Furthermore, when the total mass of the imaging apparatus attached to a mouse was 15% of the weight of the mouse, the mouse exhibited the same behavioral state as in a case where the imaging apparatus is not attached as a result of an application period of 10 to 20 minutes. Yet further, when the total mass of the imaging apparatus attached to a mouse was 20% of the weight of the mouse, the mouse exhibited the same behavioral state as in a case where the imaging apparatus is not attached as a result of an application period of 10 min/day×6 days. On the other hand, when the total mass of the imaging apparatus attached to a mouse was greater than or equal to 25% of the weight of the mouse, the mouse was unable to demonstrate basic exercise capability and stopped.

The depth of field of the observation optical system 402 is set to be deep enough that deep focus is realized. As described above, with the imaging apparatus 110, the imaging apparatus 810, or the imaging apparatus 910, an optical member for changing the progression direction of the light emitted by the light emitting unit 220 is not arranged in the cavity inside the mount section. Therefore, the observation target can be imaged with deep focus.

With the present embodiment, an optical system in which the observation target is an infinite focal point is used for imaging, and therefore the signal detection capability is improved at points where the distances from the lens are different. Furthermore, the imaging apparatus can acquire arithmetic information in the depth direction of the observation target (the up-down direction in FIG. 4, which is the extension direction of the optical axis 41) without time differences.

(Positional Relationship Between the Camera Unit 210 and the Light Emitting Unit 220)

As shown in FIGS. 4, 8, and 9, in the imaging apparatus 110, the imaging apparatus 810, and the imaging apparatus 910, on the optical axis 41, (i) the distance between the camera unit 210 and the intersection point between the optical axis 41 of the observation optical system 402 and the optical axis 42 of the illumination optical system 404 is greater than (ii) the distance between the surface of the observation window 270 on the camera unit 210 side and the camera unit 210. In other words, as seen from the camera unit 210, the intersection point between the optical axis 41 and the optical axis 42 is arranged at a farther position (sometimes referred to as a deeper position) than the surface of the observation window 270

In this way, the excitation light from the light emitting unit 220 irradiates the substantial center of the field of view of the observation target. As a result, a homogenous image having a radial altitude gradient from the center of the image, and the gradient of the excitation light irradiation intensity for the observation target is restricted.

In one embodiment, with the imaging apparatus 110, the light emitting unit 220 is arranged on one surface side of the observation window 270 (sometimes referred to as the inner surface) and radiates light toward the observation target arranged on another surface side of the observation window 270 (sometimes referred to as the outer surface. With the imaging apparatus 110, the light emitting unit 220 is arranged such that the observation target is irradiated with light from diagonally above. The light emitting unit 220 may be arranged such that the optical axis 41 of the observation optical system 402 and the optical axis 42 of the illumination optical system 404 intersect at a position farther outward than the outer surface of the observation window 270.

In this case, the angle θ formed by the optical axis 41 of the observation optical system 402 and the optical axis 42 of the illumination optical system 404 may be greater than or equal to 10° and less than or equal to 60°. This angle θ is preferably greater than or equal to 15° and less than or equal to 45°, more preferably greater than or equal to 20° and less than or equal to 40°, and even more preferably greater than or equal to 25° and less than or equal to 35°. This angle θ may be 30°.

The smaller this angle θ, the more uniform the light irradiating the observation target, but also the larger the dimensions of the hollow member 252 and the hollow member 254 in the extension direction needed to avoid interference with the camera unit 210 and the light emitting unit 220. Therefore, although it also depends on the dimensions of the camera unit 210 and the light emitting unit 220, it is possible to reduce the dimensions of the imaging apparatus 110 while restricting interference with the camera unit 210 and the light emitting unit 220 by setting the angle described above to be within the numerical range described above.

In another embodiment, with the imaging apparatus 810 and the imaging apparatus 910, the hollow pillar members forming the mount section 850 are used as the light guiding member 822 of the illumination optical system 804. With the present embodiment, the light emitting unit 220 is arranged on one inner surface side of the observation window 270. Furthermore, the light emitted by the light emitting unit 220 is radiated toward the observation target arranged on the other outer surface side of the observation window 270, via the illumination optical system 804. With the imaging apparatus 810 and the imaging apparatus 910, the illumination optical system 804 is arranged such that the observation target is irradiated with light from the horizontal direction. In this way, the optical axis of the observation optical system 402 and the optical axis of the illumination optical system 804 intersect at a position farther outward than the outer surface of the observation window 270.

In this case, the angle θ formed by the optical axis 41 of the observation optical system 402 and the optical axis of the light emitted from the illumination optical system 804 may be greater than or equal to 60° and less than or equal to 90°. This angle θ may be greater than or equal to 60° and less than or equal to 90°. This angle θ is preferably greater than or equal to 75° and less than or equal to 90°, more preferably greater than or equal to 80° and less than or equal to 90°, and even more preferably greater than or equal to 85° and less than or equal to 90°. This angle θ may be 90° (at this time, the light emitted from the illumination optical system 804 illuminates the observation target perfectly horizontally). In this way, the fluorescent light from the observation target can be observed efficiently.

The positional relationship between the camera unit 210 and the light emitting unit 220 may be determined according to the shape of the image sensor 412 or the shape of the observation target region. For example, if the planar shape of the image sensor 412 or the planar shape of the observation target region is such that the lengths thereof in two directions orthogonal to this plane are different (such a planar shape sometimes referred to as being asymmetric), the light emitting unit 220 is arranged such that the optical axis 42 of the illumination optical system 404 is inclined toward the transverse direction of the planar shape of the image sensor 412 or the optical axis 41 of the observation optical system 402.

The asymmetric shape only needs to be a shape that does not have point symmetry, and is exemplified by a shape that is linear, rectangular, elliptical, or the like. The light emitting unit 220 is arranged such that the optical axis 42 of the illumination optical system 404 is (i) substantially perpendicular to the longitudinal direction of the planar shape and (ii) inclined toward the transverse direction of the planar shape of the image sensor 412 or the observation target region.

In this case, in the imaging apparatus 110 for example, the straight line connecting the intersection point of the observation window 270 and the optical axis 41 and the intersection point of the observation window 270 and the optical axis 42 is parallel to the transverse direction of the image sensor 412 or the observation target region. In this way, even if a side illumination method is adopted as the illumination method of the imaging apparatus 110, the observation target is irradiated with more uniform light.

As described above, in the imaging apparatus 110 for example, the optical axis 42 of the illumination optical system 404 is inclined relative to the optical axis 41 of the observation optical system 402. In the example of FIG. 4, the optical axis 42 is inclined leftward in the drawing. Therefore, even if it were assumed that circular or square shaped light were emitted from the light emitting unit 220 and the light diffusing member 224, the shape of the range in which the light irradiates the observation surface (sometimes referred to as the irradiation range) is substantially elliptical or substantially rectangular. In the surface perpendicular to the optical axis 41 (e.g. the observation surface or the inner or outer surface of the observation window 270), with the direction in which the optical axis 42 is inclined being a first direction (the left-right direction in FIG. 4) and the direction orthogonal to the first direction in a plane perpendicular to the optical axis 41 described above being a second direction (the direction perpendicular to the plane of the page in FIG. 4), the longitudinal direction of the irradiation range described above is parallel to the first direction, and the transverse direction of the irradiation range described above is parallel to the second direction.

In this case, the fluctuation of the luminance in the first direction of the irradiation range is greater than the fluctuation of the luminance in the second direction of the irradiation range. Therefore, by arranging the camera unit 210 and the light emitting unit 220 such that the longitudinal direction of the irradiation range substantially matches the transverse direction of the image sensor 412 or the observation target region, the observation target is irradiated with more uniform light even if a side illumination method is adopted as the illumination method of the imaging apparatus 110.

If the observation target is irradiated with light from a plurality of light emitting units 220, at least two of the light emitting units 220 may be arranged at positions sandwiching the image sensor 412 or the observation target region. Furthermore, at least two light emitting units 220 and the image sensor 412 may be arranged such that, in the surface perpendicular to the optical axis 41, the straight line connecting the central projection position of the light emission position for the at least two light emitting units 220 and the central projection position of the image sensor 412 or the observation target region is parallel to the transverse direction of the image sensor 412 or the observation target. In this way, the observation target is irradiated with more uniform light.

The positional relationship between the camera unit 210 and the light emitting unit 220 may be determined by the type of light source of the light emitting unit 220. The type of light source can be exemplified by an LD, an LED, an organic EL, and a component in which such devices are arranged in an array. The LED may be a resonant cavity LED or a surface emitting LED.

If an LD is used as the light source, compared to using an LED as the light source, the emitted light has higher light density and a narrower wavelength region. In this way, the signal detection efficiency is improved. On the other hand, when an LED is used as the light source, the LED generates less heat than an LD, and therefore the configuration of the driver and the heat sink can be simplified and the light emitting unit 220 can be made smaller and lighter weight.

For example, in a case where the light source of the light emitting unit 220 is a laser diode (sometimes referred to as an LD), linear or elliptical light is released from the cleavage plane of the semiconductor laser forming the LD. In this case, the observation target can be uniformly illuminated by devising an arrangement method for the light emitting unit 220 at the time when the planar shape of the image sensor 412 or the planar shape of the observation target has different lengths in two directions orthogonal to each other in this plane.

More specifically, in a case where the light released from the LD is assumed to directly irradiate the surface perpendicular to the optical axis 41 (the inner surface or outer surface of the observation window 270 or the observation surface) without passing through the light diffusing member 224, the light emitting unit 220 is arranged such that the extension direction or longitudinal direction of the linear or elliptical light emitted from the LD is substantially parallel to the transverse direction of the planar shape of the observation target region or the image sensor 412. At this time, the light diffusing member 224 is actually arranged on the optical axis 42. The light diffusing member 224 may be arranged on the optical axis 42 such that the wide angle direction thereof is substantially parallel to the longitudinal direction of the planar shape of the observation target region of the image sensor 412. In this way, the observation target is irradiated with more uniform light.

There are cases where, due to the type and arrangement of the light diffusing member 224, the shape of the irradiation region has the longitudinal direction and the transverse direction switched according to whether the light diffusing member 224 is present. For example, a case can be thought of in which the light diffusing member 224 is not arranged on the optical axis 42, the linear or elliptical light is emitted from the LD of the light emitting unit 220, and a linear or elliptical irradiation range is formed on the paper 1002. In order to simplify the explanation, xy coordinates are set on the surface of the paper 1002. These xy coordinates are set such that the x direction matches the transverse direction of the irradiation region.

In this case, when the light diffusing member 224 is arranged on the optical axis 42 such that the wide angle direction of the light diffusing member 224 matches the x direction, the wide angle of the light diffusing member 224 is increased and the length of the irradiation range on the paper 1002 in the x direction is increased. Therefore, according to the size of the wide angle of the light diffusing member 224, the x direction becomes the longitudinal direction of the irradiation range and the y direction becomes the transverse direction of the irradiation range.

(Diffusion Characteristics of the Light Diffusing Member 224)

As described above, if a side illumination method is adopted as the illumination method of the imaging apparatus, it is more difficult to uniformly irradiate the observation target than in a case where a coaxial vertical illumination method is adopted. Therefore, if it is necessary to uniformly irradiate the observation target, it is preferable to use a light diffusing member 224 that has suitable diffusion characteristics to restrict the fluctuation in the luminance distribution of the irradiation range on the observation surface. The diffusion characteristics can be exemplified by diffusion transparency characteristics, diffusion reflection characteristics, and the like.

More specifically, the light diffusing member 224 preferably has a different diffusion angle for each of two direction that are orthogonal to each other and relatively high transmittance. The light diffusing member 224 having such diffusion transparency characteristics is exemplified by an LSD, a microlens array, or the like. The light diffusing member 224 may be an elliptical diffusion type of LSD. The diffusion angle of the elliptical diffusion LSD is a narrow angle of 1° to 50° or a wide angle of 30° to 95°.

The elliptical diffusion LSD can be exemplified by a 30°×1° elliptical diffusion LSD, a 30°×5° elliptical diffusion LSD, a 40°×1° elliptical diffusion LSD, a 50°×3° elliptical diffusion LSD, a 60°×1° elliptical diffusion LSD, a 60°×10° elliptical diffusion LSD, a 75°×45° elliptical diffusion LSD, a 80°×50° elliptical diffusion LSD, a 95°×25° elliptical diffusion LSD, or the like. For example, if the angle θ formed by the optical axis 41 and the optical axis 42 in the imaging apparatus 110 is greater than or equal to 25° and less than or equal to 35°, a 30°×5° elliptical diffusion LSD or a 60°×10° elliptical diffusion LSD is used.

The LSD and microlens array refract light due to the refractive action of light. Therefore, the LSD and the microlens array have excellent light transmittance compared to a diffusion plate or a white board that is manufactured through a process of embossing, chemical processing, or the like, and has a transmittance that is greater than or equal to 80%, preferably greater than or equal to 83%, more preferably greater than or equal to 85%, even more preferably greater than or equal to 88%, and even more preferably greater than or equal to 90%, for example.

As described above, if a side illumination method is adopted as the illumination method of the imaging apparatus, even if it were assumed that circular or rectangular shaped light is emitted from the light emitting unit 220 and the light diffusing member 224, the shape of the irradiation range on the observation surface is substantially elliptical or substantially rectangular. Therefore, an elliptical diffusion LSD serving as the light diffusing member 224, for example, is arranged on the optical axis of the light emitted by the light emitting unit 220.

In this way, the observation target region is irradiated more uniformly by the light from the light emitting unit 220. Furthermore, in the surface perpendicular to the optical axis 41, with the direction in which the optical axis 42 is inclined being the first direction and the direction orthogonal to the first direction in the plane perpendicular to the optical axis 41 described above being the second direction, the elliptical diffusion LSD is arranged such that the direction at which the diffusion angle of the elliptical diffusion LSD is a wide angle (sometimes referred to as the wide angle direction) is substantially parallel to the second direction and the direction at which the diffusion angle of the elliptical diffusion LSD is a narrow angle (sometimes referred to as the narrow angle direction) is substantially parallel to the first direction. The wide angle direction and the narrow angle direction may be orthogonal to each other.

If the planar shape of the image sensor 412 or the planar shape of the observation target region has lengths that are different in two directions orthogonal to each other in this plane, the elliptical diffusion LSD may be arranged such that the direction at which the diffusion angle of the elliptical diffusion LSD is a wide angle (i.e. the longitudinal direction of the light emitted from the LSD) is substantially parallel to the longitudinal direction of the image sensor 412 or the observation target region. The elliptical diffusion LSD may be an example of the light diffusing member 224.

In particular, if the light source of the light emitting unit 220 is a laser diode, linear or elliptical light is released from the cleavage surface of the semiconductor laser. In this case, there is a demand for the light diffusing member 224 to shape the linear or elliptical light into a planar shape while considering the effect of inclining the optical axis 42 relative to the optical axis 41, on the observation surface. In this case as well, by arranging the light diffusing member 224 having a different diffusion angle for each of two orthogonal directions on the optical axis of the light emitted by the light emitting unit 220, the observation target is irradiated with more uniform light.

Figure 10:
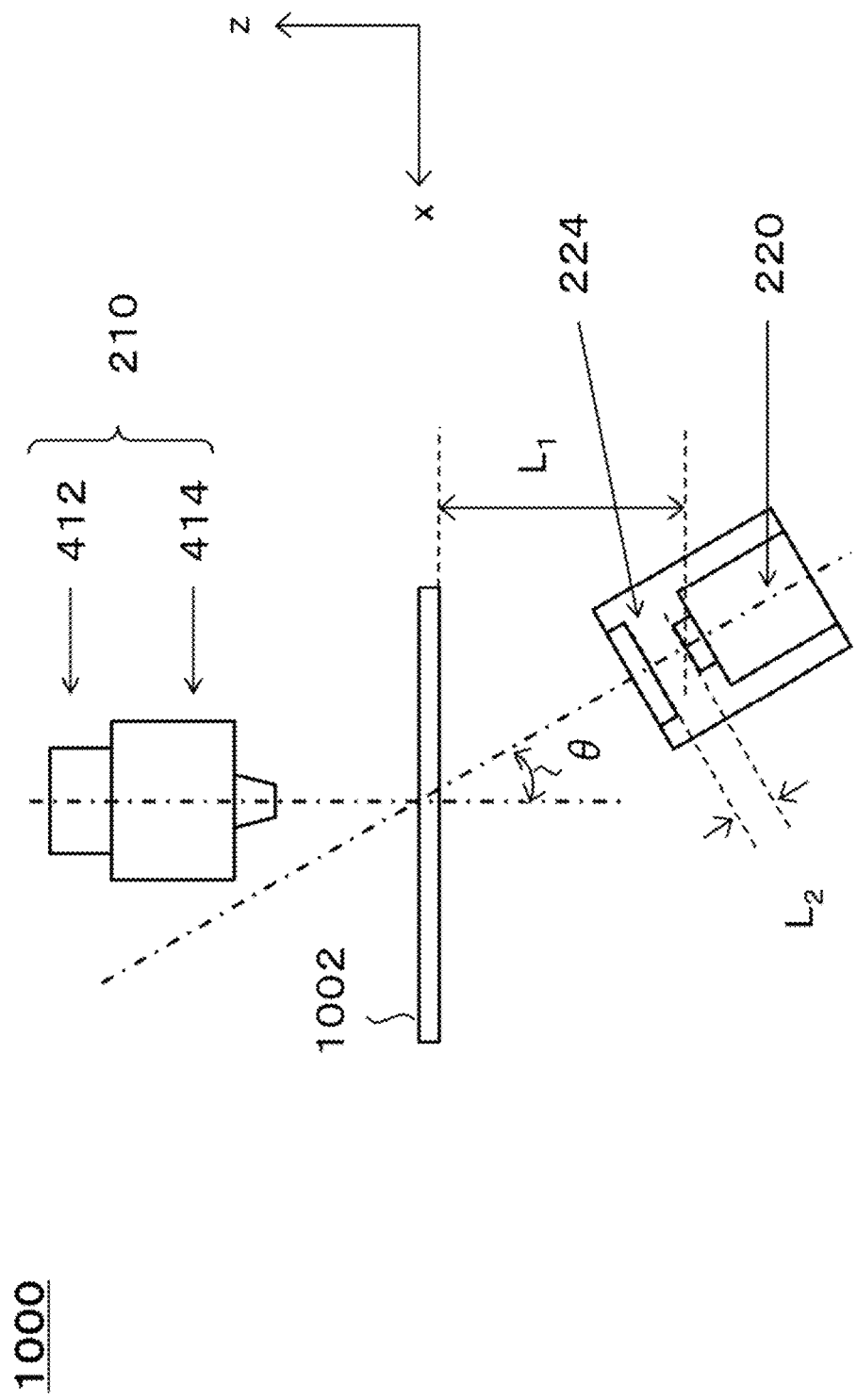
FIG. 10 schematically shows an exemplary test apparatus 1000.
Figure 14:
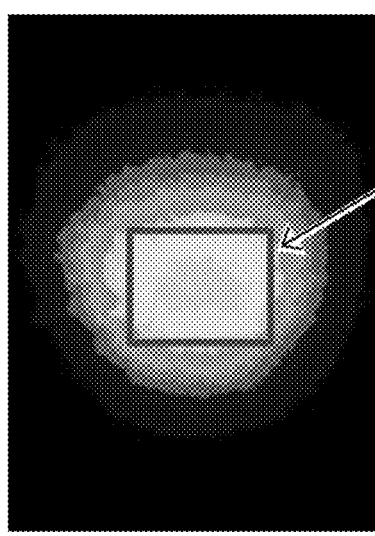
FIG. 14 shows the luminance distribution in a case where a 95°×25° elliptical diffusion LSD was used.
Figure 14:
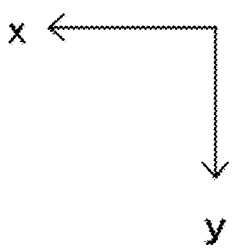
Figure 15:
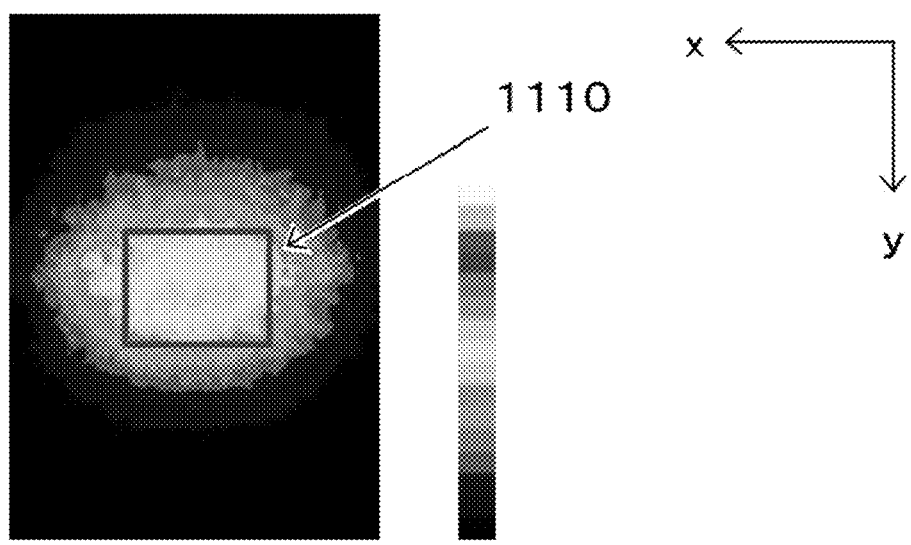
FIG. 15 shows the luminance distribution in a case where a 60°×1° elliptical diffusion LSD was used.
Figure 16:
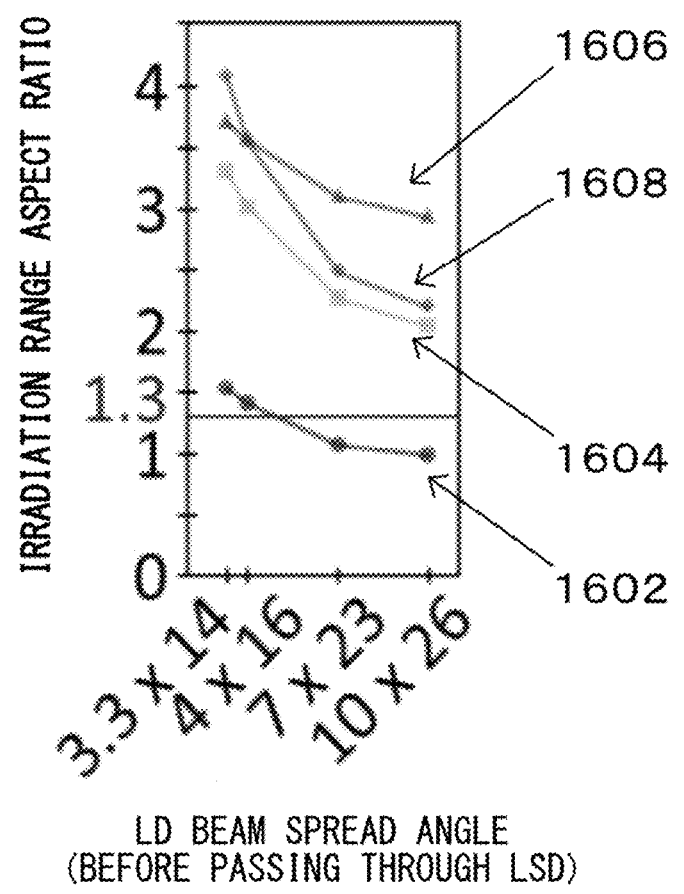
FIG. 16 shows exemplary experimental results of a verification experiment using the test apparatus 1000.
Figure 17:
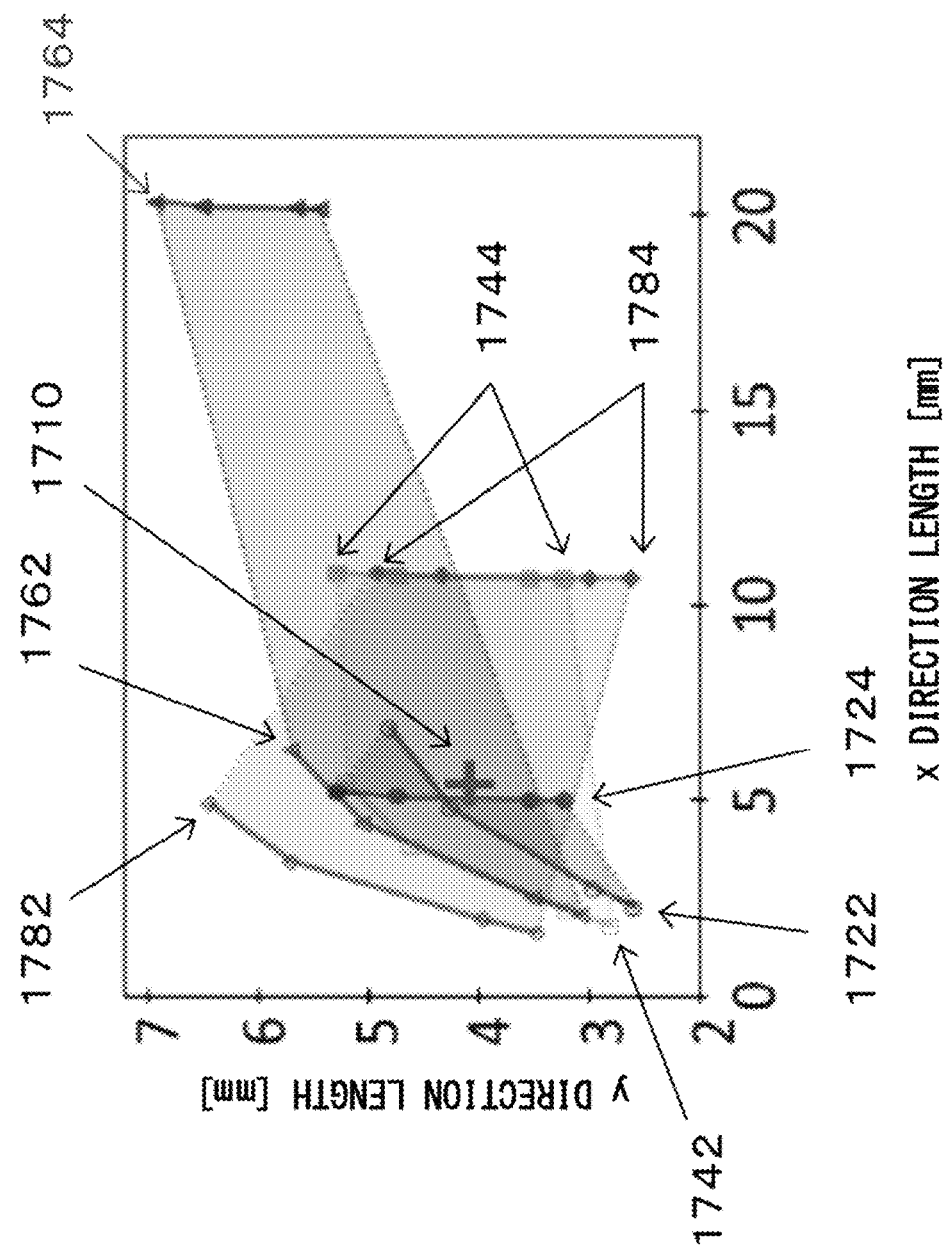
FIG. 17 shows experimental results of a verification experiment using the test apparatus 1000.

The diffusion shaping by the light diffusing member 224 is described in detail using FIGS. 10 to 17. FIG. 10 schematically shows an exemplary test apparatus 1000 for evaluating the effect of the diffusion shaping by the LSD. FIGS. 11 to 15 show measurement results of the luminance distribution obtained using the test apparatus 1000. FIGS. 16 and 17 show evaluations of the measurement results when each LSD is used.

As shown in FIG. 10, in the present embodiment, the test apparatus 1000 includes the camera unit 210, the light emitting unit 220, and the light diffusing member 224. The camera unit 210 includes the image sensor 412 and the lens unit 414. In the drawing, the x direction is the horizontal direction and the z direction is a direction vertically upward.

A laser diode (PLT5488 manufactured by OSRAM in Germany) was used as the light emitting unit 220. The oscillation threshold current of the PLT5488 is 30 mA, and the rated maximum current is 150 mA.

When the applied current was 30 mA, the beam spread angle of the PLT5488 (x direction×y direction) was 3.3°×14°. When the applied current was 40 mA, the beam spread angle of the PLT5488 was 4°×16°. When the applied current was 75 mA, the beam spread angle of the PLT5488 was 7°×23°. When the applied current was 150 mA, the beam spread angle of the PLT5488 was 10°×26°.

A digital camera (COOLPIX P7100 manufactured by Nikon Corporation) was used as the camera unit 210. A 30°×5° elliptical diffusion LSD (LSD 30×5PC10 manufactured by Optical Solutions Corporation), a 60°×10° elliptical diffusion LSD (LSD 60×10PC10 manufactured by Optical Solutions Corporation), a 95°×25° elliptical diffusion LSD (LSD 95×25PC10 manufactured by Optical Solutions Corporation), and a 60°×1° elliptical diffusion LSD (LSD 60×1PC10 manufactured by Optical Solutions Corporation) were used as the light diffusing member 224.

In the present embodiment, the light emitting unit 220 radiates light toward paper 1002 held horizontally, from below the paper 1002. The camera unit 210 measures the luminance distribution on the paper 1002 serving as the observation surface, from above the paper 1002. The angle θ formed by the optical axis of the camera unit 210 and the optical axis of the light emitting unit 220 was set to be 30°. In other words, the camera unit 210 and the light emitting unit 220 were arranged such that the optical axis of the light emitting unit 220 was inclined 30° in the x direction from the optical axis of the camera unit 210. The distance $L_1$ between the light emitting unit 220 and the bottom surface of the paper 1002 was set to 8 mm. When an LSD was used as the light diffusing member 224, the distance $L_2$ between the LSD and the light emitting unit 220 was set to 1 mm.

Next, the details of the measurement results of the luminance distribution obtained when the applied current was 40 mA are described using FIGS. 11 to 15. In FIGS. 11 to 15, the observation target region 1110 has a rectangular shape that is 4.0 mm×5.3 mm. The planar shape of the observation target region 1110 may be similar to the planar shape of the image sensor. In the present embodiment, the longitudinal direction of the observation target region 1110 matches the x direction in the drawing. The transverse direction of the observation target region 1110 matches the y direction in the drawing. In the present embodiment, the light is radiated from the right towards the left.

Figure 11:
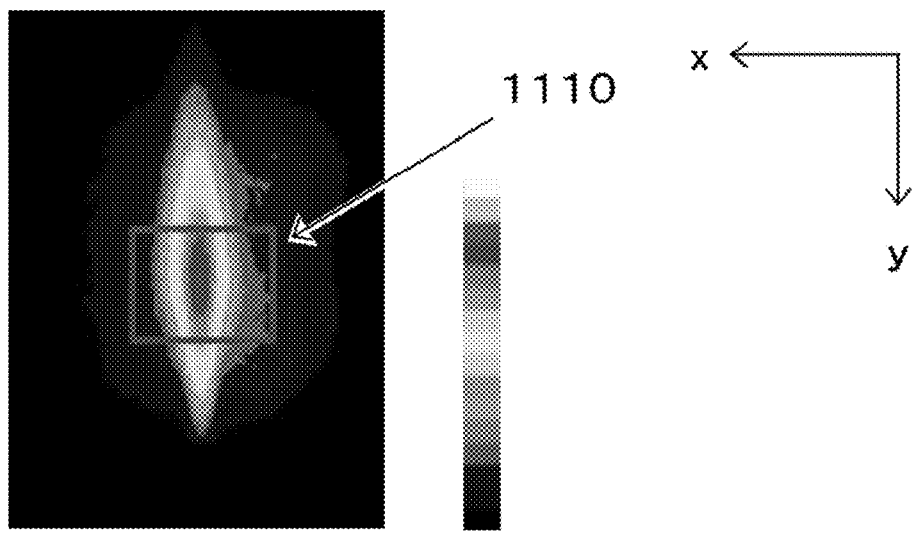
FIG. 11 shows the luminance distribution in a case where no LSD was provided.
Figure 12:
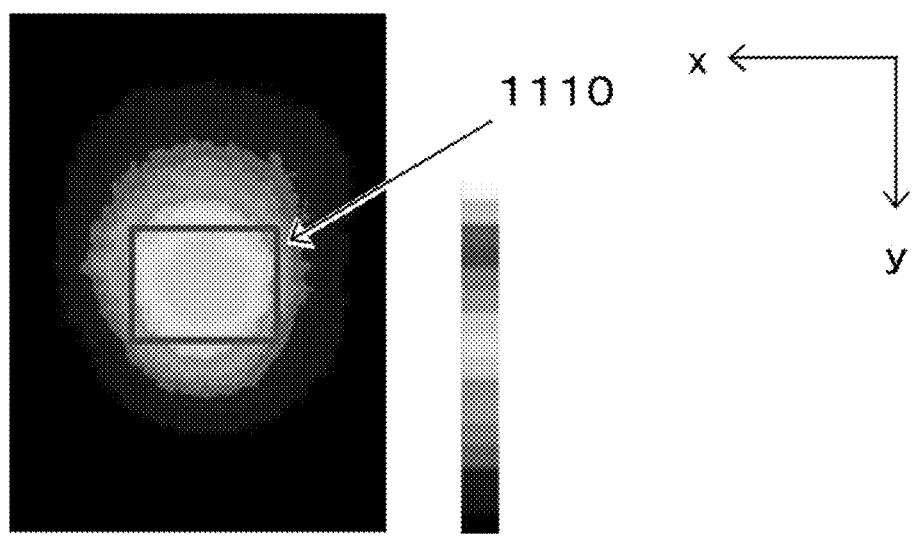
FIG. 12 shows the luminance distribution in a case where a 30°×5° elliptical diffusion LSD was used.
Figure 13:
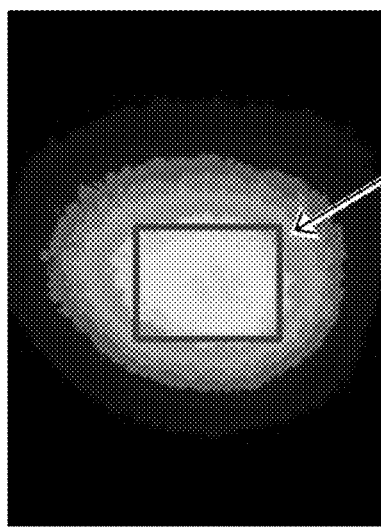
FIG. 13 shows the luminance distribution in a case where a 60°×10° elliptical diffusion LSD was used.
Figure 13:
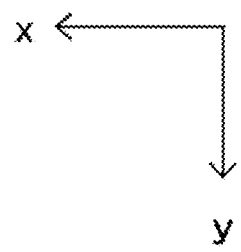

FIG. 11 shows the luminance distribution in a case where no LSD was provided as the light diffusing member 224. FIG. 12 shows the luminance distribution in a case where a 30°×5° elliptical diffusion LSD was used. FIG. 13 shows the luminance distribution in a case where a 60°×10° elliptical diffusion LSD was used. FIG. 14 shows the luminance distribution in a case where a 95°×25° elliptical diffusion LSD was used. FIG. 15 shows the luminance distribution in a case where a 60°×1° elliptical diffusion LSD was used.

As shown in FIG. 11, with the present embodiment, the transverse direction of the illumination range caused by the LD and the longitudinal direction of the observation target region 1110 are substantially parallel, Furthermore, as shown in FIG. 11, when no LSD is provided, there is a large amount of luminance fluctuation inside the observation target region 1110. On the other hand, as shown in FIGS. 12 to 15, when an elliptical diffusion LSD is provided on the optical axis 42, the length of the observation target region 1110 in the x direction is increased, compared to the experimental results of FIG. 11. Furthermore, the illumination within the observation target region 1110 is more uniform than in the experimental results of FIG. 11.

FIG. 16 shows exemplary experimental results of a verification experiment using the test apparatus 1000. FIG. 16 shows the fluctuation of the aspect ratio of the diffusion angle, which accompanies the fluctuation of the current value applied to the LD (PLT5488 manufactured by OSRAM in Germany) of the test apparatus 1000 in a case where each type of LSD is used. In FIG. 16, the horizontal axis indicates the angle of the beam spread of the light emitted from the LD. The angle of the beam spread of the emitted light was adjusted by changing the applied current. Each experimental result was plotted using the length in the transverse direction of the light emitted from the LD as a reference. For example, the data indicating the aspect ratio in a case where the beam spread angle (x direction×y direction) is "3.3×14" is plotted at the position of 3.3° on the horizontal axis. Similarly, the data in a case where the beam spread angle is "4×16" is plotted at the position of 4° on the horizontal axis. The data in a case where the beam spread angle is "7×23" is plotted at the position of 7° on the horizontal axis. The data in a case where the beam spread angle is "10×26" is plotted at the position of 10° on the horizontal axis.

In FIG. 16, the vertical axis indicates the aspect ratio of the diffusion angle of the light irradiating the paper 1002, after the light is emitted from the LD and the LSD is machined. As described above, the angle formed by the paper 1002 and the plane perpendicular to the optical axis 42 of the LD was 30°. The aspect ratio described above was calculated by dividing the length in the longitudinal direction of the shape of the light projected onto the paper 1002 by the length in the transverse direction of the shape of this light. Furthermore, the imaging region of the CMOS arranged in the camera unit 210 was 640×480 pixels, and the aspect ratio of this CMOS was 1.33 (indicated by horizontal lines in the drawing).

In FIG. 16, the curve 1602 indicates the aspect ratio in a case where the 30°×5° elliptical diffusion LSD was used. The curve 1604 indicates the aspect ratio in a case where the 60°×10° elliptical diffusion LSD was used. The curve 1606 indicates the aspect ratio in a case where the 95°×25° elliptical diffusion LSD was used. The curve 1608 indicates the aspect ratio in a case where the 60°×1° elliptical diffusion LSD was used.

According to FIG. 16, in a case where the 30°×5° elliptical diffusion LSD was used as a condition of the test apparatus 1000, the aspect ratio described above is understood to remain at a value near 1.33 regardless of the applied current value. Furthermore, in a case where the 60°×10° elliptical diffusion LSD was used, it is understood that relatively favorable results are obtained.

FIG. 17 shows trial calculations relating to the dimensions of the irradiation range of the light irradiating the paper 1002 in a case where each type of LSD was used. In FIG. 17, the cross-shaped mark 1710 indicates the dimensions of the observation target region 1110 (the x direction is 5.3 mm and the y direction is 4.0 mm) described in relation to FIGS. 11 to 15. As shown in FIGS. 11 to 15, the shape of the observation target region 1110 is rectangular.

In FIG. 17, the curve 1722 and the curve 1724 show the change in the dimensions of the irradiation range when the applied current was changed to 30 mA, 40 mA, 75 mA, and 110 mA, in a case where the 30°×5° elliptical diffusion LSD was used. FIG. 12 described above shows an exemplary luminance distribution in a case where the 30°×5° elliptical diffusion LSD was used and the applied current was 40 mA.

The curve 1722 indicates the dimensions (sometimes referred to as the half-value dimensions) of the region where the luminance level is the half-value of the highest luminance in the luminance distribution obtained using the test apparatus 1000. The curve 1724 indicates the dimensions (sometimes referred to as maximum dimensions) of the irradiation range on the paper 1002, calculated theoretically based on the shape of the light emitted by the LD (sometimes referred to as the original shape), the specifications relating to the diffusion angle of each LSD, and the specifications of the test apparatus 1000. The dimensions of the irradiation range realizing enough luminance to observe the observation target depend on the intensity of the light emitted by the LD, but are greater than or equal to the half-value dimensions and less than or equal to the maximum dimensions, for example.

In FIG. 17, the curve 1742 and the curve 1744 show the change in the dimensions of the irradiation range when the applied current was changed to 30 mA, 40 mA, 75 mA, and 110 mA, in a case where the 60°×10° elliptical diffusion LSD was used. The curve 1742 shows the fluctuation of the half-value dimensions, and the curve 1744 shows the fluctuation of the maximum dimensions.

In FIG. 17, the curve 1762 and the curve 1764 show the change in the dimensions of the irradiation range when the applied current was changed to 30 mA, 40 mA, 75 mA, and 110 mA, in a case where the 95°×25° elliptical diffusion LSD was used. The curve 1762 shows the fluctuation of the half-value dimensions, and the curve 1764 shows the fluctuation of the maximum dimensions.

In FIG. 17, the curve 1782 and the curve 1784 show the change in the dimensions of the irradiation range when the applied current was changed to 30 mA, 40 mA, 75 mA, and 110 mA, in a case where the 60°×1° elliptical diffusion LSD was used. The curve 1782 shows the fluctuation of the half-value dimensions, and the curve 1784 shows the fluctuation of the maximum dimensions.

The specifications of the LSD and the applied current of the LD may be determined using FIG. 17. For example, according to FIG. 17, concerning the conditions of the test apparatus 1000, it is understood that the observation target region that is 4.0 mm×5.3 mm is covered in all cases except when the 30°×5° elliptical diffusion LSD is used. Furthermore, it is possible to determine the setting range of the applied current in a case where each LSD is used, from FIG. 17. In another embodiment, it is possible to use the 30°×5° elliptical diffusion LSD in a case where the dimensions of the observation target region 1110 differ from those of the present embodiment. For example, the 30°×5° elliptical diffusion LSD may be used in a case where the dimensions of the observation target region 1110 are 2.5 mm×3.3 mm.

(Thermal Transfer Countermeasures in the Imaging Apparatus)

Figure 18:
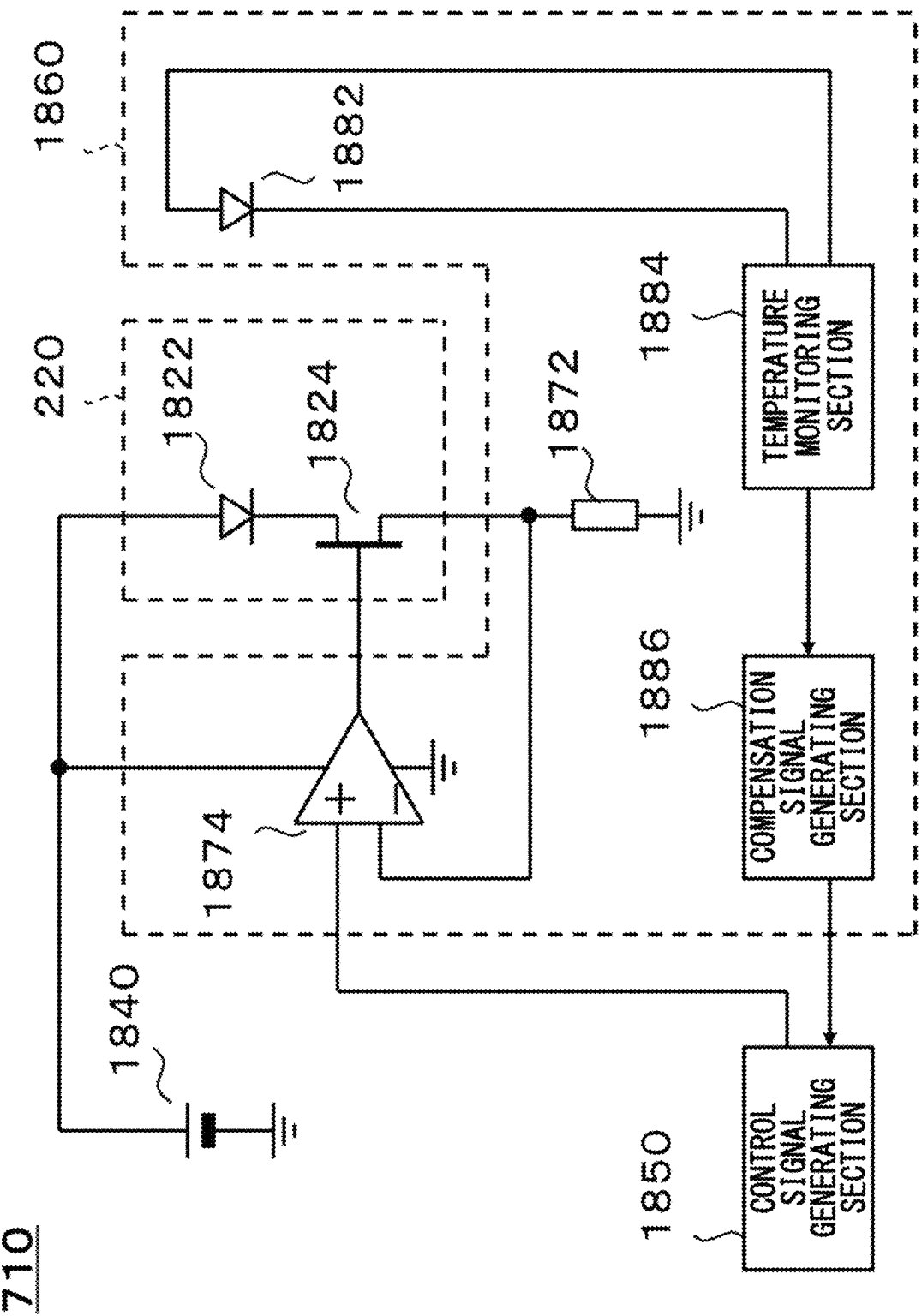
FIG. 18 schematically shows an exemplary internal configuration of the drive control section 710.

FIG. 18 schematically shows an exemplary internal configuration of the drive control section 710, along with an exemplary light emitting unit 220. In the present embodiment, the light emitting unit 220 includes a laser diode 1822 and a drive transistor 1824.

In the present embodiment, the drive control section 710 includes a power source 1840, a control signal generating section 1850, and a compensating section 1860. In the present embodiment, the compensating section 1860 includes a resistor 1872 and an operational amplifier 1874. Furthermore, the compensating section 1860 includes a temperature sensor 1882, a temperature monitoring section 1884, and a compensation signal generating section.

The laser diode 1822 may be an example of a light emitting section. The drive control section 710 may be an example of a control section. The control signal generating section 1850 may be an example of a pulse signal generating section.

In the present embodiment, the laser diode 1822 emits light. One end of the laser diode 1822 may be electrically connected to the power source 1840. The other end of the laser diode 1822 may be electrically connected to one end of the drive transistor 1824.

In the present embodiment, the drive transistor 1824 controls the current flowing through the laser diode 1822. The drive transistor 1824 may control the current flowing through the laser diode 1822 based on the control signal from the control signal generating section 1850. More specifically, the drive transistor 1824 may control the current flowing through the laser diode 1822 based on the signal from the operational amplifier 1874. In this way, the drive transistor 1824 can control the driving of the laser diode 1822.

One end of the drive transistor 1824 may be electrically connected to the other end of the laser diode 1822. The other end of the drive transistor 1824 may be electrically connected to one end of the resistor 1872.

The type of transistor that can be used as the drive transistor 1824 is not particularly limited. The drive transistor 1824 is exemplified by a bipolar transistor, an electrical field effect transistor, and the like. Instead of the drive transistor 1824, a type of switching element that is not a transistor may be used. The transistor may be an example of a switching element.

In the present embodiment, the power source 1840 supplies power to the laser diode 1822. The power source 1840 may supply power to the operational amplifier 1874.

In the present embodiment, the control signal generating section 1850 generates the control signal for controlling the drive of the laser diode 1822. The control signal generating section 1850 may supply the operational amplifier 1874 with the generated control signal. For example, the control signal generating section 1850 generates a pulse signal causing the laser diode 1822 to intermittently emit light. The frequency of the switching between ON/OFF for the pulse signal is set so as to not have a significant effect on the imaging of the observation target.

The control signal generating section 1850 may generate this pulse signal such that the temperature of the light emitting unit 220 becomes less than a predetermined value. The control signal generating section 1850 may generate this pulse signal such that the temperature of the light emitting unit 220 falls within a predetermined numerical range.

With the present embodiment, the light emitting unit 220 is controlled by the pulse signal generated by the control signal generating section 1850. In this way, the light emitting unit 220 intermittently emits light. As a result, heat generation by the light emitting unit 220 is restricted, compared to a case where the light emitting unit 220 continuously emits light.

The control signal generating section 1850 may determine the duty ratio of the pulse signal, according to the heat dissipation ability of the light emitting unit 220. For example, the control signal generating section 1850 generates the pulse signal such that the duty ratio of the pulse signal is larger when the heat dissipation ability of the light emitting unit 220 is greater.

The control signal generating section 1850 may determine the value of the applied current that is applied to the light emitting unit 220 indicated by the pulse signal according to the heat dissipation ability of the light emitting unit 220. For example, the control signal generating section 1850 generates the pulse signal such that the applied current value indicated by the pulse signal is larger when the heat dissipation ability of the light emitting unit 220 is greater.

In the present embodiment, the compensating section 1860 controls the control signal generating section 1850 such that the temperature of the light emitting unit 220 becomes less than a predetermined value. When the temperature of the laser diode 1822 remains high, it is easy for problems such as a decrease in the amount of emitted light, shortening of the lifespan, and damage to occur in the laser diode 1822. Therefore, an upper limit temperature during operation is set for the laser diode 1822, and the drive control section 710 drives the laser diode 1822 such that the temperature of the laser diode 1822 does not exceed the upper limit temperature.

For example, the compensating section 186 acquires information indicating the temperature or heat generation amount of the light emitting unit 220 or laser diode 1822. The compensating section 1860 generates the compensation signal indicating the amount of temperature compensation, such that the temperature of the light emitting unit 220 is less than the predetermined value. The compensating section 1860 transmits the compensation signal to the control signal generating section 1850.

In the present embodiment, the resistor 1872 is used to detect the current flowing through the drive transistor 1824. One end of the resistor 1872 may be electrically connected to the other end of the drive transistor 1824. The other end of the resistor 1872 may be grounded.

In the present embodiment, the operational amplifier 1874 controls the current (sometimes referred to as the drive current) flowing through the laser diode 1822. For example, the operational amplifier 1874 determines the drive current of the laser diode 1822 such that the voltage across the terminals of the resistor 1872 and the input voltage caused by the control signal from the control signal generating section 1850 become equal.

The control signal from the control signal generating section 1850 may be input to the non-inverting input terminal of the operational amplifier 1874. The control signal may be a pulse drive signal. The voltage at the connection point between the drive transistor 1824 and the resistor 1872 is input to the inverting input terminal of the operational amplifier 1874. The output terminal of the operational amplifier 1874 is electrically connected to the base or gate of the drive transistor 1824. In this way, the drive current of the laser diode 1822 is controlled such that the voltage across the terminals of the resistor 1872 and the input voltage caused by the control signal from the control signal generating section 1850 become equal.

In the present embodiment, the temperature sensor 1882 measures the temperature of the laser diode 1822. The temperature sensor 1882 may detect that the temperature of the laser diode 1822 has exceeded a predetermined value. The temperature sensor 1882 may output, to the temperature monitoring section 1884, a signal indicating the temperature of the laser diode 1822 or a signal indicating that the temperature of the laser diode 1822 has exceeded the predetermined value.

The temperature measurement method or detection method is not particularly limited. In one embodiment, the temperature of the laser diode 1822 is measured by a sensor thermally coupled to the laser diode 1822. This sensor is exemplified by a thermistor, a posistor, a thermocouple, a temperature reference diode, a non-contact thermometer, or the like.

In the present embodiment, the temperature monitoring section 1884 monitors the temperature of the laser diode 1822. The temperature monitoring section 1884 may monitor the temperature of the laser diode 1822 based on the output from the temperature sensor 1882. For example, when the temperature of the laser diode 1822 has exceeded the predetermined value, the temperature monitoring section 1884 may output, to the compensation signal generating section 1886, the signal indicating the temperature of the laser diode 1822 or the signal indicating that the temperature of the laser diode 1822 has exceeded the predetermined value.

In the present embodiment, the temperature monitoring section 1884 is described in detail using an example of a case in which the temperature monitoring section 1884 monitors the temperature of the laser diode 1822 based on the output from the temperature sensor 1882. However, the temperature monitoring section 1884 is not limited to the present embodiment.

In another embodiment, the temperature monitoring section 1884 may monitor the temperature of the laser diode 1822 based on a measured value of the forward drop voltage of the laser diode 1822. In yet another embodiment, the temperature monitoring section 1884 may monitor the temperature of the laser diode 1822 based on a relationship between the emitted light intensity and the drive current of the laser diode 1822. Generally, when the temperature of a laser diode rises, the forward drop voltage of the laser diode decreases. Furthermore, if the laser diode is driven with a constant current, the emitted light intensity of the laser diode decreases when the temperature of the laser diode rises.

In the present embodiment, the compensation signal generating section 1886 acquires, from the temperature monitoring section 1884, a signal indicating the temperature of the laser diode 1822 or a signal indicating that the temperature of the laser diode 1822 has exceeded a first value. The compensation signal generating section 1886 generates the compensation signal indicating the amount of temperature compensation such that the temperature of the light emitting unit 220 becomes less than a predetermined second value. The second value may be the same as or different from the first value. The second value may be less than the first value. The compensation signal generating section 1886 may include a hysteresis circuit. The compensation signal generating section 1886 transmits the compensation signal to the control signal generating section 1850.

For example, when the temperature of the laser diode 1822 has exceeded the first value, the compensation signal generating section 1886 transmits, to the control signal generating section 1850, a compensation signal indicating a decrease in the reference voltage of the control signal. The compensation signal may include information indicating the amount of the decrease in the reference voltage. When the control signal generating section 1850 outputs the control signal based on the compensation signal described above, the drive current of the laser diode 1822 is decreased and the temperature of the laser diode 1822 drops.

When the temperature of the laser diode 1822 has become less than the second value, the compensation signal generating section 1886 transmits, to the control signal generating section 1850, a compensation signal indicating the return of the reference voltage of the control signal to the original value or a compensation signal indicating an increase of the reference voltage of the control signal. The compensation signal may include information indicating the amount of the increase of the reference voltage. In this way, the light amount of the laser diode 1822 is recovered.

Figure 19:
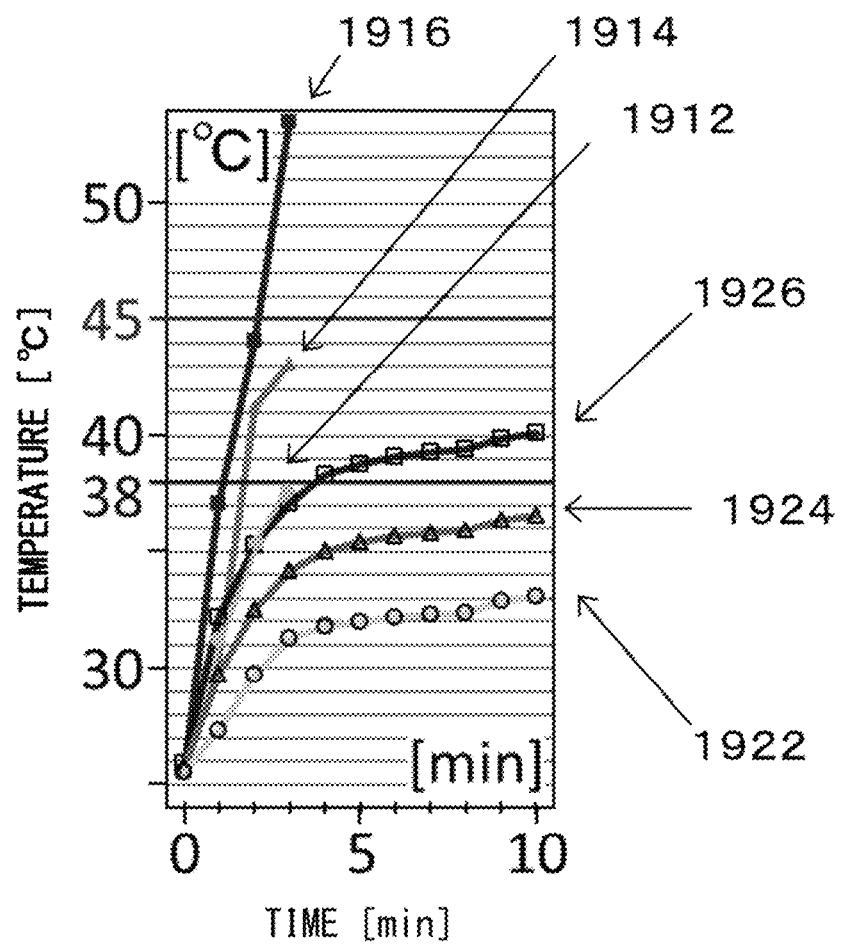
FIG. 19 shows the temperature change of an LD when a heat dissipation board was not provided.
Figure 20:
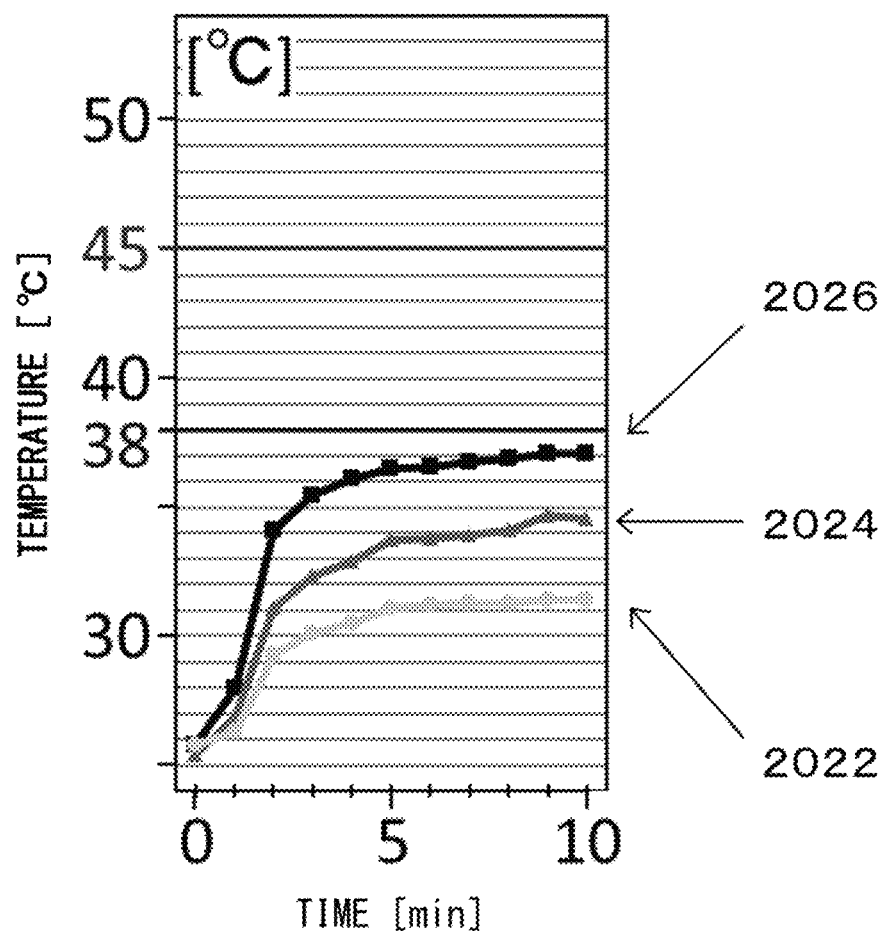
FIG. 20 shows the temperature change of an LD when a 146.7 mm$^2$ heat dissipation board was used.
Figure 21:
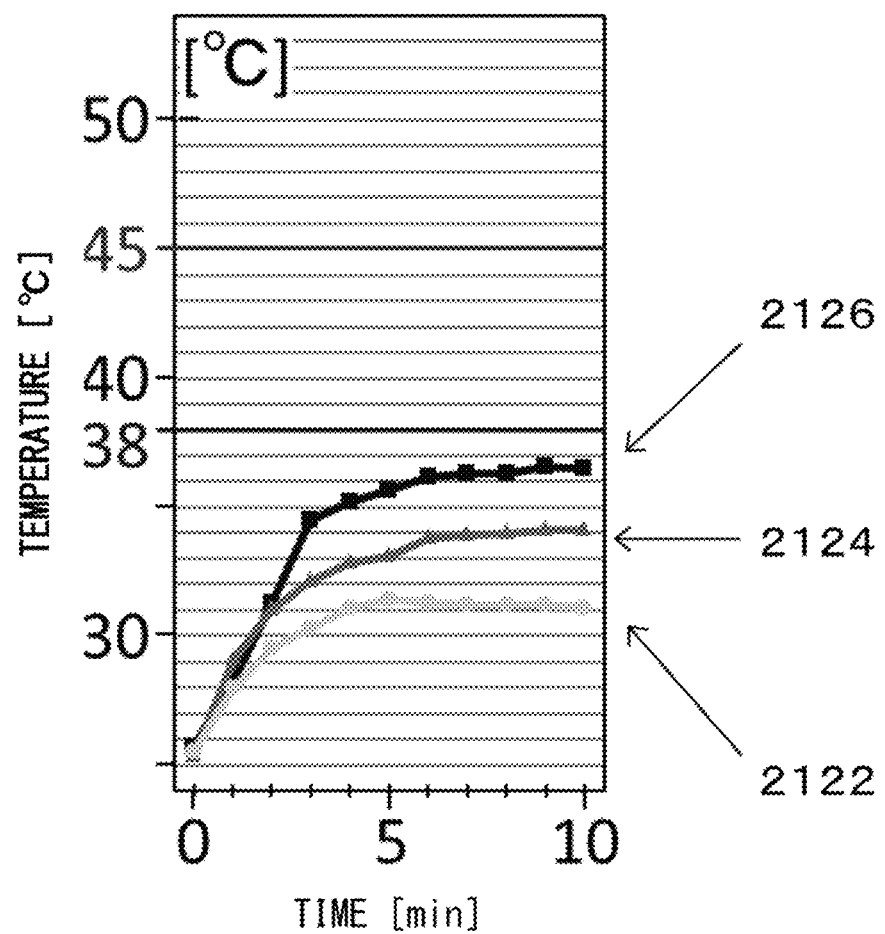
FIG. 21 shows the temperature change of an LD when a 194.7 mm$^2$ heat dissipation board was used.
Figure 22:
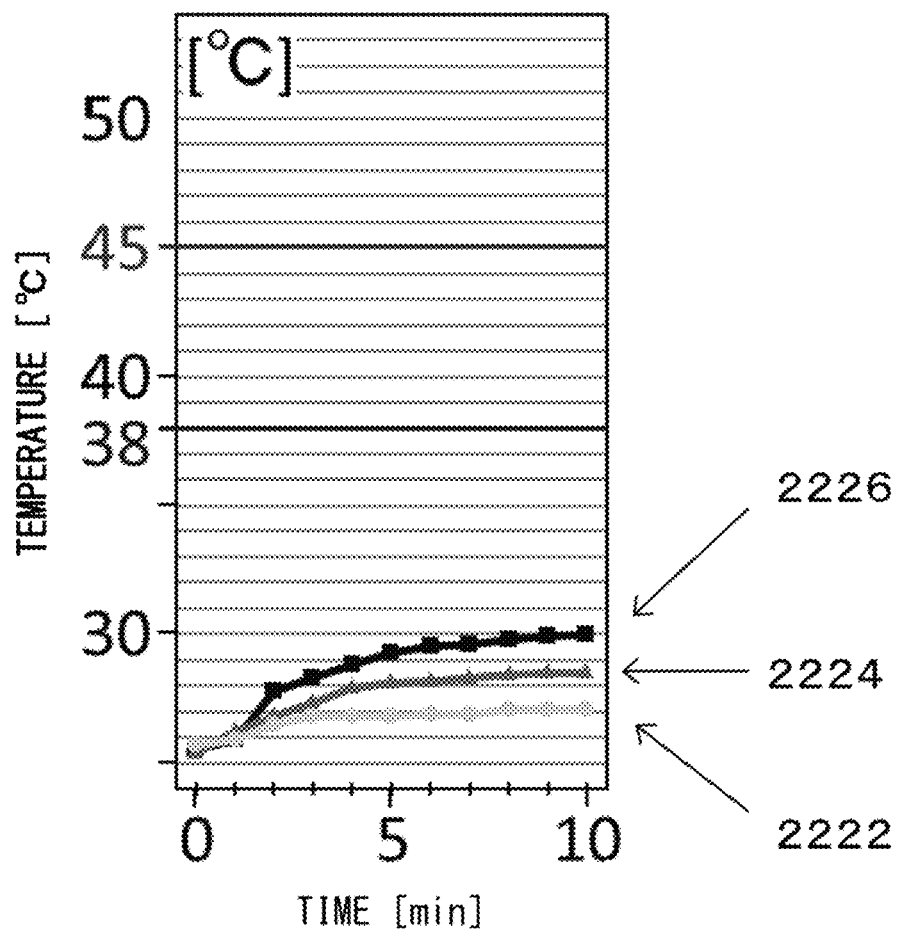
FIG. 22 shows the temperature change of an LD when an 889.2 mm$^2$ heat dissipation board was used.

An example of a heat dissipation test is described using FIGS. 19 to 22. FIG. 19 shows the temperature change of an LD when a heat dissipation board was not provided. FIG. 20 shows the temperature change of an LD when a 146.7 mm$^2$ heat dissipation board was used. FIG. 21 shows the temperature change of an LD when a 194.7 mm$^2$ heat dissipation board was used. FIG. 22 shows the temperature change of an LD when an 889.2 mm$^2$ heat dissipation board was used. In each of FIGS. 19 to 22, the vertical axis indicates the temperature of the metal chassis of the laser diode (PL450B manufactured by OSRAM in Germany) and the horizontal axis indicates time.

In the heat dissipation tests of FIGS. 19 to 22, a copper cover 230 was used. In this way, it was possible to use the cover 230 as a portion of the heat dissipation board and wiring. The material of the cover 230 that can be used as a portion of the heat dissipation board and wiring is not limited to copper. In another embodiment, a cover 230 made of silver, aluminum, or iron may be used.

Specifically, a notch was formed in a portion of the opening 232 of the cover 230, such that the opening 232 is deformed by external force. After a laser diode (PL450B manufactured by OSRAM in Germany) was arranged inside the opening 232, the laser diode was secured to the cover 230 by applying an external force to reduce the size of the opening 232. After this, the laser diode was connected to a power source by using the cover 230 as a portion of the wiring.

The oscillation threshold current of the PL450B was 30 mA, and the maximum optical output power was 100 mW. The temperature of the metal chassis of the PL450B was measured using a thermocouple. When considering that the body temperature of a mouse is 38° C. and the temperature at which irreversible damage to a cell occurs is 45° C., the temperature of the PL450B is preferably kept at less than or equal to 45° C., and more preferably kept at less than or equal to 38° C.

FIG. 19 shows the temperature change of an LD in a case where a heat dissipation board is not provided. The curve 1912 indicates the temperature change of an LD in a case where a current of 60 mA is continuously applied. The curve 1914 indicates the temperature change of an LD in a case where a current of 100 mA is continuously applied. The curve 1916 indicates the temperature change of an LD in a case where a current of 145 mA is continuously applied.

The curve 1922 indicates the temperature change of an LD in a case where a current of 60 mA is applied intermittently with a frequency of 32 kHz. The curve 1924 indicates the temperature change of an LD in a case where a current of 80 mA is applied intermittently with a frequency of 32 kHz. The curve 1926 indicates the temperature change of an LD in a case where a current of 120 mA is applied intermittently with a frequency of 32 kHz.

FIG. 20 shows the temperature change of an LD in a case where a heat dissipation board made of copper and having a surface area of 146.7 mm$^2$ was attached to the cover 230. The curve 2022 indicates the temperature change of the LD in a case where a current of 60 mA is applied intermittently with a frequency of 32 kHz. The curve 2024 indicates the temperature change of the LD in a case where a current of 80 mA is applied intermittently with a frequency of 32 kHz. The curve 2026 indicates the temperature change of the LD in a case where a current of 120 mA is applied intermittently with a frequency of 32 kHz.

FIG. 21 shows the temperature change of an LD in a case where a heat dissipation board made of copper and having a surface area of 194.7 mm$^2$ was attached to the cover 230. The curve 2122 indicates the temperature change of the LD in a case where a current of 60 mA is applied intermittently with a frequency of 32 kHz. The curve 2124 indicates the temperature change of the LD in a case where a current of 80 mA is applied intermittently with a frequency of 32 kHz. The curve 2126 indicates the temperature change of the LD in a case where a current of 120 mA is applied intermittently with a frequency of 32 kHz.

FIG. 22 shows the temperature change of an LD in a case where a heat dissipation board made of copper and having a surface area of 889.2 mm$^2$ was attached to the cover 230. The curve 2222 indicates the temperature change of the LD in a case where a current of 60 mA is applied intermittently with a frequency of 32 kHz. The curve 2224 indicates the temperature change of the LD in a case where a current of 80 mA is applied intermittently with a frequency of 32 kHz. The curve 2226 indicates the temperature change of the LD in a case where a current of 120 mA is applied intermittently with a frequency of 32 kHz.

From FIGS. 19 to 22, it is understood that heat generation of an LD can be restricted by intermittently turning ON the LD using a pulse signal. Furthermore, it is understood that heat generation of the LD can be further restricted by attaching a thermal dissipation board to the cover 230.

(Countermeasures for Stray Light in the Mount Section)

As described with reference to FIG. 5, in one embodiment, the hollow member of the mount section or the inner surface of the hollow member is coated with a light absorbent material that absorbs light with a wavelength approximately equal to the wavelength of the light emitted by the light emitting unit 220, or with a reflection restricting material that restricts the reflection of this light. This light absorbing material or light reflecting material can be exemplified by (i) paint, ink, or soot used for a coating process, (ii) an antireflective coating material, or the like. In another embodiment, a structure for restricting the reflection of light with a wavelength approximately equal to that of the light emitted by the light emitting unit 220 is arranged on the inner surface of the hollow member of the mount section or the inner surface of the hollow member. The structure for restricting the reflection of light can be exemplified by an antireflection sheet, bristles for antireflection, or a shading plate for stray light prevention.

In this way, it is possible to restrict the light emitted by the light emitting unit 220 from progressing into the mount section or being detected by the camera unit 210 after being reflected by the observation target. As a result, noise caused by the reflected light from the observation target can be reduced.

For example, in a case where the excitation light for exciting the observation target is emitted by the light emitting unit 220 and the camera unit 210 receives the fluorescent light from the observation target, the excitation light from the light emitting unit 220 is reflected by the surface of the observation target, and there is a possibility that the this light is detected by the camera unit 210. However, according to the present embodiment, the excitation light reflected by the surface of the observation target is restricted from progressing into the inside of the mount section. Furthermore, even in a case where the excitation light reflected by the surface of the observation target progresses into the inside of the mount section, reflection of this excitation light inside the mount section is restricted, and this excitation light is absorbed within the mount section. In this way, the excitation light reflected by the surface of the observation target is restricted from being detected by the camera unit 210. As a result, the camera unit 210 can observe the fluorescent light from the observation light in a state where there is little noise.

While the embodiment(s) of the present invention has (have) been described, the technical scope of the invention is not limited to the above described embodiment(s). It is apparent to persons skilled in the art that various alterations and improvements can be added to the above-described embodiment(s). It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

LIST OF REFERENCE NUMERALS

10: mouse, 100: biometric information gathering system, 110: imaging apparatus, 120: relay apparatus, 122: jacket, 130: information processing apparatus, 210: camera unit, 212: cable, 214: optical filter, 220: light emitting unit, 222: cable, 224: light diffusing member, 230: cover, 232: opening, 240: seal member, 250: mount section, 252: hollow member, 254: hollow member, 262: opening: 264: opening, 266: opening, 270: observation window, 332: protruding portion, 352: protruding portion, 380: binding band, 41: optical axis, 42: optical axis, 402: observation optical system, 404: illumination optical system, 412: image sensor, 414: lens unit, 450: overload prevention member, 452: cable, 502: cavity, 550: thermal insulation member, 650: thermal insulation member, 710: drive control section, 720: A/D converting section, 730: data processing section, 740: communication control section, 804: illumination optical system, 810: imaging apparatus, 822: light guiding member, 826: mirror member, 828: concave portion, 850: mount section, 910: imaging apparatus, 940: seal member, 948: through-hole, 1000: test apparatus, 1002: paper, 1110: observation target region, 1602: curve, 1604: curve, 1606: curve, 1608: curve, 1710: mark, 1722: curve, 1724: curve, 1742: curve, 1744: curve, 1762: curve, 1764: curve, 1782: curve, 1784: curve, 1822: laser diode, 1824: drive transistor, 1840: power source, 1850: control signal generating section, 1860: compensating section, 1872: resistor, 1874: operational amplifier, 1882: temperature sensor, 1884: temperature monitoring section, 1886: compensation signal generating section, 1912: curve, 1914: curve, 1916: curve, 1922: curve, 1924: curve, 1926: curve, 2022: curve, 2024: curve, 2026: curve, 2122: curve, 2124: curve, 2126: curve, 2222: curve, 2224: curve, 2226: curve

What is claimed is:

1. A light detecting apparatus comprising:
a light emitting section configured to emit light;
a light detecting section configured to detect light from an observation target irradiated with the light emitted by the light emitting section;
a mount section attached to a test subject that includes the observation target;
a holding section configured to hold the light emitting section and the light detecting section and is detachably attached to the mount section;
an illumination optical system configured to guide the light emitted by the light emitting section to the observation target; and
an observation optical system configured to guide light from the observation target to the light detecting section, wherein
the holding section is configured to hold the light emitting section and the light detecting section to secure a relative positional relationship between the light emitting section and the light detecting section,
a relative positional relationship between the holding section and the mount section is determined by attaching the holding section to the mount section,
the illumination optical system includes a diffusion member configured to diffuse the light emitted by the light emitting section,
an angle formed by an optical axis of the illumination optical system and an optical axis of the observation optical system is greater than 0° and less than 90°,
a cavity or light guiding member penetrating through the mount section is arranged inside the mount section,
the light emitting section is configured such that the light emitted from the light emitting section passes through the cavity or the light guiding member, is emitted from a surface of the mount section facing the observation target, and arrives at the observation target,
the light detecting section is configured such that the light from the observation target is incident to the cavity or the light guiding member from the surface of the mount section facing the observation target, passes through the cavity or the light guiding member, and arrives at the light detecting section,
the cavity is arranged inside the mount section, and
an opening for inserting a tool inside the cavity from outside the mount section is formed in the mount section.

2. The light detecting apparatus according to claim 1, wherein
at least one of the holding section and the mount section includes a positioning section configured to determine the relative positional relationship between the holding section and the mount section when the holding section is attached to the mount section.

3. The light detecting apparatus according to claim 1, wherein
the relative positional relationship between the light emitting section and the light detecting section is determined such that reflected light, which is light from the light emitting section reflected inside the cavity or the light guiding member does not directly arrive at the light detecting section.

4. The light detecting apparatus according to claim 1, wherein
at least one of the light emitting section and the light detecting section is arranged inside the cavity.

5. The light detecting apparatus according to claim 1, wherein
the light detecting section is configured to detect fluorescent light from the observation target that has been excited by the light emitted by the light emitting section, and the light detecting apparatus further comprises a first optical member that is arranged in an optical path of the fluorescent light from the observation target, wherein a transmittance of the first optical member of light is greater at a peak wavelength of the fluorescent light from the observation target than at a peak wavelength of the light emitted by the light emitting section.

6. The light detecting apparatus according to claim 1, wherein
the holding section includes a heat dissipation board configured to release heat generated by the light emitting section.

7. The light detecting apparatus according to claim 1, wherein
thermal conductivity of a main component of the holding section is greater than thermal conductivity of a main component of the mount section.

8. The light detecting apparatus according to claim 1, further comprising:
a thermal insulation member that is arranged between the holding section and the mount section, and configured to restrict movement of heat from the holding section to the mount section.

9. A light detecting apparatus comprising:
a light emitting section configured to emit light;
a light detecting section configured to detect light from an observation target irradiated with the light emitted by the light emitting section;
a mount section attached to a test subject that includes the observation target;
a holding section configured to hold the light emitting section and the light detecting section and is detachably attached to the mount section;
an illumination optical system configured to guide the light emitted by the light emitting section to the observation target; and
an observation optical system configured to guide light from the observation target to the light detecting section, wherein
the holding section is configured to hold the light emitting section and the light detecting section to secure a relative positional relationship between the light emitting section and the light detecting section,
a relative positional relationship between the holding section and the mount section is determined by attaching the holding section to the mount section,
the illumination optical system includes a diffusion member configured to diffuse the light emitted by the light emitting section, and
an angle formed by an optical axis of the illumination optical system and an optical axis of the observation optical system is greater than 0° and less than 90°, wherein
the mount section has an outer shape resulting from a second hollow pillar member connecting integrally with an outer circumference of a first hollow pillar member,
a cross-sectional area of the second hollow pillar member, when cleaved on a plane perpendicular to an extension direction thereof, is less than a cross-sectional area of the first hollow pillar member, when cleaved on a plane perpendicular to an extension direction thereof,
an angle formed by a central axis of the first hollow pillar member and a central axis of the second hollow pillar member is greater than 0° and less than or equal to 90°, and
an empty hole of the first hollow pillar member and an empty hole of the second hollow pillar member are in communication inside the mount section.

10. The light detecting apparatus according to claim 9, wherein
the mount section has an outer shape resulting from a plurality of the second hollow pillar members connecting integrally with the outer circumference of the first hollow pillar member, and
the empty hole of the first hollow pillar member and the empty hole of each of the plurality of second hollow pillar members are in communication inside the mount section.

11. The light detecting apparatus according to claim 9, wherein
the light emitting section is configured to irradiate the observation target with light via a hollow portion of the second hollow pillar member, and
the light detecting section is configured to receive the light from the observation target via a hollow portion of the first hollow pillar member.

12. The light detecting apparatus according to claim 1, wherein
the mount section is secured to a surface of the test subject that includes the observation target, or at least a portion of the mount section is embedded inside the test subject.

13. The light detecting apparatus according to claim 1, further comprising:
a control section configured to control emission of light in the light emitting section, wherein
the control section includes a pulse signal generating section configured to generate a pulse signal causing the light emitting section to intermittently emit light such that a temperature of the light emitting section becomes less than a predetermined value.

14. The light detecting apparatus according to claim 1, wherein
the diffusion member has a different diffusion angle for each of two directions that are orthogonal to each other.

15. A light detecting apparatus according comprising:
a light emitting section configured to emit light;
a light detecting section configured to detect light from an observation target irradiated with the light emitted by the light emitting section;
a mount section attached to a test subject that includes the observation target;
a holding section configured to hold the light emitting section and the light detecting section and is detachably attached to the mount section;
an illumination optical system configured to guide the light emitted by the light emitting section to the observation target; and
an observation optical system configured to guide light from the observation target to the light detecting section, wherein
the holding section is configured to hold the light emitting section and the light detecting section to secure a relative positional relationship between the light emitting section and the light detecting section,
a relative positional relationship between the holding section and the mount section is determined by attaching the holding section to the mount section,
the illumination optical system includes a diffusion member configured to diffuse the light emitted by the light emitting section, and an angle formed by an optical axis of the illumination optical system and an optical axis of the observation optical system is greater than 0° and less than 90°, wherein a shape of the light detecting section or the observation target is asymmetrical, an optical axis of the illumination optical system is inclined toward a transverse direction of the light detecting section or the observation target, from an optical axis of the observation optical system, a diffusion angle of the diffusion member is wider in a wide angle direction than in a direction orthogonal to the wide angle direction, and the diffusion member is arranged on an optical path of the light emitted by the light emitting section, such that the wide angle direction of the diffusion member is substantially parallel to a longitudinal direction of the light detecting section or the observation target.

16. The light detecting apparatus according to claim 1, wherein mass of the light detecting apparatus is less than 3 g.

17. The light detecting apparatus according to claim 1, wherein mass of the light detecting apparatus is less than 1 g.

18. A biometric information acquiring apparatus, comprising:

the light detecting apparatus according to claim 1;

a drive control section configured to drive the light emitting section; and a data processing section configured to process a detection signal generated based on the light detected by the light detecting section.

\* \* \* \* \*